(12) United States Patent
Wilson et al.

(10) Patent No.: US 9,795,478 B2
(45) Date of Patent: Oct. 24, 2017

(54) INVERSION DELIVERY DEVICE AND METHOD FOR A PROSTHESIS

(71) Applicant: HLT, Inc., Maple Grove, MN (US)

(72) Inventors: Robert Foster Wilson, Roseville, MN (US); Cassandra Ann Piippo Svendsen, Minneapolis, MN (US); Dale K. Nelson, Inver Grove Heights, MN (US); John P. Gainor, Mendota Heights, MN (US)

(73) Assignee: HLT, Inc., Maple Grove, MN (US)

( * ) Notice: Subject to any disclaimer, the term of this patent is extended or adjusted under 35 U.S.C. 154(b) by 383 days.

(21) Appl. No.: 14/270,300

(22) Filed: May 5, 2014

(65) Prior Publication Data

US 2014/0243962 A1 Aug. 28, 2014

Related U.S. Application Data

(63) Continuation of application No. 13/657,800, filed on Oct. 22, 2012, now Pat. No. 9,522,064, which is a continuation-in-part of application No. 13/473,475, filed on May 16, 2012, now abandoned.

(60) Provisional application No. 61/486,682, filed on May 16, 2011.

(51) Int. Cl.
*A61F 2/24* (2006.01)
*A61F 2/95* (2013.01)

(52) U.S. Cl.
CPC .......... *A61F 2/2439* (2013.01); *A61F 2/2418* (2013.01); *A61F 2/2427* (2013.01); *A61F 2/2436* (2013.01); *A61F 2002/9517* (2013.01); *A61F 2002/9534* (2013.01)

(58) Field of Classification Search
CPC .... A61F 2/2436; A61F 2/2427; A61F 2/2439; A61F 2002/9517; A61F 2002/9534
See application file for complete search history.

(56) References Cited

U.S. PATENT DOCUMENTS

| | | |
|---|---|---|
| 5,261,916 A | 11/1993 | Engelson |
| 5,843,261 A | 12/1998 | Abraham, Jr. |
| 5,846,261 A | 12/1998 | Kotula et al. |
| 6,016,810 A | 1/2000 | Ravenscroft |

(Continued)

FOREIGN PATENT DOCUMENTS

| | | |
|---|---|---|
| DE | 102005052628 A1 | 5/2007 |
| JP | 2002-537943 A | 11/2002 |

(Continued)

OTHER PUBLICATIONS

State Intellectual Property Office, P.R. China, First Office Action dated Oct. 28, 2015 with English translation in Chinese Patent Application No. 201280074609.2, 16 pages.

(Continued)

*Primary Examiner* — Ashley Fishback
(74) *Attorney, Agent, or Firm* — Inskeep IP Group, Inc.

(57) ABSTRACT

A delivery device usable to deliver an inverting implant is provided that includes a positioning mechanism that automatically initiates the inversion process once a predetermined length of the implant has exited a delivery catheter. The positioning mechanism allows the implant to be safely and accurately deployed with reduced operator experience and in a greater variety of target locations.

7 Claims, 22 Drawing Sheets

(56) References Cited

U.S. PATENT DOCUMENTS

| | | | |
|---|---|---|---|
| 6,126,686 | A | 10/2000 | Badylak et al. |
| 6,168,614 | B1 | 1/2001 | Andersen et al. |
| 6,524,339 | B1 | 2/2003 | Adams |
| 6,592,614 | B2 | 7/2003 | Lenker et al. |
| 6,719,781 | B1 | 4/2004 | Kim |
| 7,329,279 | B2 | 2/2008 | Haug et al. |
| 7,374,571 | B2 | 5/2008 | Pease et al. |
| 7,479,155 | B2 | 1/2009 | Gainor et al. |
| 8,118,866 | B2 | 2/2012 | Herrmann et al. |
| 8,778,019 | B2 | 7/2014 | Knippel et al. |
| 2002/0032481 | A1 | 3/2002 | Gabbay |
| 2004/0024416 | A1 | 2/2004 | Yodfat et al. |
| 2004/0073293 | A1 | 4/2004 | Thompson |
| 2004/0220664 | A1 | 11/2004 | Chobotov |
| 2004/0260333 | A1 | 12/2004 | Dubrul et al. |
| 2005/0137702 | A1 | 6/2005 | Haug et al. |
| 2005/0222674 | A1 | 10/2005 | Paine |
| 2005/0283231 | A1 | 12/2005 | Haug et al. |
| 2006/0058872 | A1 | 3/2006 | Salahieh et al. |
| 2006/0271166 | A1 | 11/2006 | Thill et al. |
| 2008/0082165 | A1 | 4/2008 | Wilson et al. |
| 2008/0208328 | A1 | 8/2008 | Antocci et al. |
| 2009/0012553 | A1 | 1/2009 | Swain et al. |
| 2009/0076598 | A1 | 3/2009 | Salahieh et al. |
| 2009/0222076 | A1 | 9/2009 | Figulla et al. |
| 2009/0254165 | A1 | 10/2009 | Tabor et al. |
| 2010/0121434 | A1 | 5/2010 | Paul et al. |
| 2010/0286658 | A1 | 11/2010 | Stalker et al. |
| 2012/0095550 | A1 | 4/2012 | Gainor |
| 2012/0245606 | A1* | 9/2012 | Goldberg ............... A61B 17/11 606/153 |

FOREIGN PATENT DOCUMENTS

| | | |
|---|---|---|
| JP | 2003-506133 A | 2/2003 |
| JP | 2004-503327 A1 | 2/2004 |
| WO | WO00/53120 A1 | 9/2000 |
| WO | WO02/05729 A2 | 1/2002 |
| WO | WO03/092554 A1 | 11/2003 |
| WO | WO2005009285 | 2/2005 |
| WO | WO2008072838 | 6/2008 |
| WO | WO2008103497 | 8/2008 |
| WO | WO2010033698 | 3/2010 |
| WO | WO2011143263 | 11/2011 |

OTHER PUBLICATIONS

U.S., Office Action dated Aug. 26, 2013 in U.S. Appl. No. 11/443,814, 5 pages.
Japanese Patent Office, Office Action dated Jul. 25, 2013 in Japanese Patent Application No. JP2012-108576, 1 page.
U.S., Office Action dated Jul. 3, 2013 in U.S. Appl. No. 13/192,375, 9 pages.
European Patent Office, Supplementary European Search Report dated Jun. 13, 2013 in European Patent Application No. EP06771666, 7 pages.
U.S., Office Action dated Jun. 12, 2013 in U.S. Appl. No. 13/458,023, 8 pages.
Japanese Patent Office, Notice of Allowance dated May 31, 2013 in Japanese Patent Application No. JP2008-513838, 3 pages.
IP Australia, Notice of Acceptance mailed Mar. 25, 2013 in Australian Patent Application No. AU2011265440, 3 pages.
U.S., Interview Summary dated Feb. 22, 2013 in U.S. Appl. No. 13/458,023, 3 pages.
U.S., Interview Summary dated Feb. 22, 2013 in U.S. Appl. No. 11/443,814, 3 pages.
European Patent Office, Examination Report dated Feb. 14, 2013 in European Patent Application No. EP06771666, 3 pages.
WIPO, U.S. International Search Authority, International Search Report and Written Opinion dated Feb. 1, 2013 in International Patent Application No. PCT/US2012/061393, 10 pages.
Japanese Patent Office, Office Action dated Jan. 28, 2013 with English translation in Japanese Patent Application No. JP2008-513838, 11 pages.
State Intellectual Property Office, P.R. China, Notification to Go Through Formalities of Registration mailed Jan. 4, 2013 in Chinese Patent Application No. CN201010533068 with English translation, 5 pages.
Canadian Intellectual Property Office, Office Action dated Dec. 6, 2012 in Canadian Patent Application No. CA2613958, 3 pages.
U.S., Office Action dated Nov. 14, 2012 in U.S. Appl. No. 11/443,814, 11 pages.
U.S., Office Action dated Nov. 13, 2012 in U.S. Appl. No. 13/458,023, 11 pages.
WIPO, U.S. International Search Authority, International Search Report and Written Opinion dated Sep. 7, 2012 in International Patent Application No. PCT/US2012/038205, 17 pages.
IP Australia, Examination Report dated Jul. 16, 2012 in Australian Patent Application No. AU2011265440, 3 pages.
State Intellectual Property Office, P.R. China, Office Action dated Jun. 1, 2012 with English translation in Chinese Patent Application No. CN201010533068.8, 4 pages.
Japanese Patent Office, Office Action dated May 2, 2012 with English translation in Japanese Patent Application No. JP2008-513838, 4 pages.
Japanese Patent Office, Office Action dated Sep. 28, 2011 in Japanese Patent Application No. JP2008-513838, 7 pages.
IP Australia, Notice of Acceptance dated Sep. 15, 2011 in Australian Patent Application No. AU2006251938, 3 pages.
State Intellectual Property Office, P.R. China, First Office Action dated Nov. 27, 2009 in Chinese Patent Application No. CN201010533068.8, 4 pages.
IP Australia, Examiner's Report dated Apr. 18, 2011 in Australian Patent Application No. AU2006251938, 2 pages.
U.S., Final Office Action dated Dec. 14, 2010 in U.S. Appl. No. 11/443,814, 10 pages.
State Intellectual Property Office, P.R. China, Notification to Go Through Formalities of Registration mailed Aug. 3, 2010 in Chinese Patent Application No. CN200680027512 with English translation, 5 pages.
U.S., Final Office Action dated Jul. 22, 2011 in U.S. Appl. No. 11/443,814, 9 pages.
U.S., Interview Summary dated May 3, 2010 in U.S. Appl. No. 11/443,814, 3 pages.
U.S., Office Action dated Dec. 20, 2009 in U.S. Appl. No. 11/443,814, 7 pages.
State Intellectual Property Office, P.R. China, Examiner's Report dated Nov. 27, 2009 in Chinese Patent Application No. CN200680027512.0, 6 pages.
U.S., Office Action dated Apr. 17, 2009 in U.S. Appl. No. 11/443,814, 7 pages.
U.S., Final Office Action dated Nov. 17, 2008 in U.S. Appl. No. 11/443,814, 10 pages.
U.S., Office Action dated Mar. 18, 2008 in U.S. Appl. No. 11/443,814, 10 pages.
WIPO, U.S. International Preliminary Examining Authority, International Preliminary Report on Patentability dated Nov. 30, 2007 in International Patent Application No. PCT/US2006/021021, 7 pages.
WIPO, U.S. International Search Authority, International Search Report and Written Opinion dated Sep. 5, 2007 in International Patent Application No. PCT/US2006/021021, 10 pages.
European Patent Office, European Partial Search Report dated Feb. 23, 2015 in European Patent Application No. 12876788.6, 5 pages.
European Patent Office, European Extended Search Report dated Jun. 12, 2015 in European Patent Application No. 12876788.6, 9 pages.
European Patent Office, European Extended Search Report dated Sep. 16, 2014 in European Patent Application No. 12785404.0, 7 pages.
Japanese Patent Office, Office Action dated Dec. 4, 2015 in Japanese Patent Application No. 2014-511500, 4 pages.

* cited by examiner

INVERSION DELIVERY DEVICE AND METHOD FOR A PROSTHESIS

RELATED APPLICATIONS

This application is a continuation of U.S. patent application Ser. No. 13/657,800 filed Oct. 22, 2012, entitled Inversion Delivery Device And Method For A Prosthesis, which is a Continuation-In-Part of U.S. patent application Ser. No. 13/473,475, filed on May 16, 2012, entitled Inversion Delivery Device and Method for a Prosthesis, which claims priority to U.S. Provisional Application Ser. No. 61/486,682 filed May 16, 2011 entitled Inversion Delivery Device and Method For A Prosthesis, which is hereby incorporated herein by reference in its entirety.

BACKGROUND OF THE INVENTION

There has been a significant movement toward developing and performing cardiovascular surgeries using a percutaneous approach. Through the use of one or more catheters that are introduced through, for example, the femoral artery, tools and devices can be delivered to a desired area in the cardiovascular system to perform many number of complicated procedures that normally otherwise require an invasive surgical procedure. Such approaches greatly reduce the trauma endured by the patient and can significantly reduce recovery periods. The percutaneous approach is particularly attractive as an alternative to performing open-heart surgery.

Valve replacement surgery provides one example of an area where percutaneous solutions are being developed. A number of diseases result in a thickening, and subsequent immobility or reduced mobility, of heart valve leaflets. Such immobility also may lead to a narrowing, or stenosis, of the passageway through the valve. The increased resistance to blood flow that a stenosed valve presents can eventually lead to heart failure and ultimately death.

Treating valve stenosis or regurgitation has heretofore involved complete removal of the existing native valve through an open-heart procedure followed by the implantation of a prosthetic valve. Naturally, this is a heavily invasive procedure and inflicts great trauma on the body leading usually to great discomfort and considerable recovery time. It is also a sophisticated procedure that requires great expertise and talent to perform.

Historically, such valve replacement surgery has been performed using traditional open-heart surgery where the chest is opened, the heart stopped, the patient placed on cardiopulmonary bypass, the native valve excised and the replacement valve attached. A proposed percutaneous valve replacement alternative method on the other hand, is disclosed in U.S. Pat. No. 6,168,614 (the entire contents of which are hereby incorporated by reference) issued to Andersen et al. In this patent, the prosthetic valve is mounted on a stent that is collapsed to a size that fits within a catheter. The catheter is then inserted into the patient's vasculature and moved so as to position the collapsed stent at the location of the native valve. A deployment mechanism is activated that expands the stent containing the replacement valve against the valve cusps. The expanded structure includes a stent configured to have a valve shape with valve leaflet supports begins to take on the function of the native valve. As a result, a full valve replacement has been achieved but at a significantly reduced physical impact to the patient.

However, this approach has decided shortcomings. One particular drawback with the percutaneous approach disclosed in the Andersen '614 patent is the difficulty in preventing leakage around the perimeter of the new valve after implantation. Since the tissue of the native valve remains within the lumen, there is a strong likelihood that the commissural junctions and fusion points of the valve tissue (as pushed apart and fixed by the stent) will make sealing around the prosthetic valve difficult. In practice, this has often led to severe leakage of blood around the stent apparatus.

Other drawbacks of the Andersen '614 approach pertain to its reliance on stents as support scaffolding for the prosthetic valve. First, stents can create emboli when they expand. Second, stents are typically not effective at trapping the emboli they dislodge, either during or after deployment. Third, stents do not typically conform to the features of the native lumen in which they are placed, making a prosthetic valve housed within a stent subject to paravalvular leakage. Fourth, stents are subject to a tradeoff between strength and compressibility. Fifth, stents cannot be retrieved once deployed. Sixth, stents have an inherent strength that is not adjustable.

As to the first drawback, stents usually fall into one of two categories: self-expanding stents and balloon expandable stents. Self-expanding stents are compressed when loaded into a catheter and expand to their original, non-compressed size when released from the catheter. These are typically made of Nitinol. Balloon expandable stents are loaded into a catheter in a compressed but relaxed state. These are typically made from stainless steel or other malleable metals. A balloon is placed within the stent. Upon deployment, the catheter is retracted and the balloon inflated, thereby expanding the stent to a desired size. Both of these stent types exhibit significant force upon expansion. The force is usually strong enough to crack or deform thrombosis, thereby causing pieces of atherosclerotic plaque to dislodge and become emboli. If the stent is being implanted to treat a stenosed vessel, a certain degree of such expansion is desirable. However, if the stent is merely being implanted to displace native valves, less force may be desirable to reduce the chance of creating emboli. An additional concern related to displacing an aortic valve is the risk of conduction disturbances (i.e. left bundle branch block) due to the close proximity of the conduction pathways to the native valve structure. Excessive radial force applied at the native valve site increases the risk of irritation or damage to the conduction pathway and heart block.

As to the second drawback, if emboli are created, expanded stents usually have members that are too spaced apart to be effective to trap any dislodged material. Often, secondary precautions must be taken including the use of nets and irrigation ports.

The third drawback is due to the relative inflexibility of stents. Stents typically rely on the elastic nature of the native vessel to conform around the stent. Stents used to open a restricted vessel do not require a seal between the vessel and the stent. However, when using a stent to displace native valves and house a prosthetic valve, a seal between the stent and the vessel is necessary to prevent paravalvular leakage. Due to the non-conforming nature of stents, this seal is hard to achieve, especially when displacing stenosed valve leaflets.

The fourth drawback is the tradeoff between compressibility and strength. Stents are made stronger or larger by manufacturing them with thicker members. Stronger stents are thus not as compressible as weaker stents. Most stents suitable for use in a valve are not compressible enough to be placed in a thin catheter, such as a 18 Fr catheter. Larger delivery catheters are more difficult to maneuver to a target area and also result in more trauma to the patient.

The fifth drawback of stents is that they are not easily retrievable. Once deployed, a stent may not be recompressed and drawn back into the catheter for repositioning due to the non-elastic deformation (stainless steel) or the radial force required to maintain the stent in place (Nitinol). Thus, if a physician is unsatisfied with the deployed location or orientation of a stent, there is little he or she can do to correct the problem.

The sixth drawback listed above is that stents have an inherent strength and are thus not adjustable. As previously stated, stronger stents are made with stronger members. Once a stent is selected and deployed, there is little a physician can do if the stent proves to be too strong or too weak.

Various embodiments of devices that solve these problems are introduced in U.S. Patent Publication No. 2006/0271166 to Thill et al., entitled "Stentless Support Structure," the contents of which is incorporated herein in their entirety. This publication teaches a braided mesh tube that is capable of folding back and forth into itself to build, in situ, a support structure that is strong enough to hold back the leaflets of a native valve sufficiently to successfully deploy a replacement valve, thus obviating the need for excision of the native valve. Advantageously, because of the inverting nature of these devices, the braided mesh, in an elongated delivery configuration, does not need to possess the strength to accomplish native valve displacement until the inversion process occurs. This allows the mesh tube to be constructed such that, in the elongated delivery state, the tube can be compressed into a very small catheter, such as a 18 Fr or smaller catheter. Such a small catheter significantly reduces patient trauma and allows for easy percutaneous, intraluminal navigation through the blood vessels. It is to be understood that terms like transluminal and percutaneous, as used herein, are expressly defined as navigation to a target location through and axially along the lumen of a blood vessel or blood vessels as opposed to surgically cutting the target vessel or heart open and installing the device manually. It is further to be understood that the term "mesh" as used herein describes a material constructed of one or more braided or woven strands.

In order to accomplish the folding back and forth feature of this device, there are preformed, circumferential folds in the device. One embodiment has two circumferential folds that are longitudinally spaced apart in the extended configuration. One of these folds is preformed to fold inwardly, and the other is preformed to fold outwardly. These preformed folds, when released out of a catheter, tend to return to a folded configuration that has a z-like cross-section. This cross-section design results not only because the inward pre-formed fold folds inwardly and the outward pre-formed fold folds outwardly, but because these folds reverse longitudinal positions once folded. If the inward preformed fold is distal of the outward preformed fold in the extended position, in the folded position the inward preformed fold will be proximal of the outward preformed fold. This design allows a valve on a distal end of the device to be drawn into the device when folded, without requiring the valve itself to be inverted or everted. In one embodiment having two preformed folds, the inversion process thus results in a three-layered configuration that could be significantly shorter than the extended length, depending on the spacing of the folds.

In the development of the devices described in the aforementioned publication, U.S. Pat. Pub. 2006/0271166, it was found that, occasionally, it was advantageous to use an additional device to hold the outermost layer of the implant axially in place while inversion of a layer was being effected. This gave rise to the delivery tool shown and described in U.S. Patent Publication 2008/0082165 to Wilson et al., entitled "Delivery Tool For Percutaneous Delivery Of A Prosthesis." This delivery tool includes an expandable mesh region that, when axially compressed, flares outwardly to form a bulbous or rounded structure of increased radius. Further axial compression creates a flat, disc-like surface. In use, the device is extended through an implant prior to releasing the implant from the delivery catheter. The device is then expanded to the disc-like configuration and pulled proximally to act as a backstop at a desired target location, against which the implant is delivered. Thus, the disc-like device prevents axial migration of the implant in a distal direction if and when distal force is placed on the implant during inversion of the second or subsequent layers into the first layer.

It has been found, however, that in some cases, depending on target location and patient anatomy, there is insufficient space in a distal axial direction beyond the target location to efficiently use this delivery device. For example, some patients may have limited left ventricular space, which may prohibit the use of the backstop device.

There is thus a need for a device that is able to prevent axial migration of the aforementioned braided implant devices during inversion, but does not require significant space distally beyond the target location.

BRIEF SUMMARY OF THE INVENTION

The present invention meets the identified need by providing a delivery device that holds a braided implant in a desired location during inversion of a subsequent layer into a first layer. More specifically, the present invention provides a delivery device that releasably attaches at or near a first fold location, hereinafter referred to as the "aortic flare," which is a hinge point around which the inversion of the implant used with the present invention occurs.

Through attachment to the aortic flare, the delivery device of the present invention enables precise positioning and inversion by limiting advancement of a portion of the implant while continuing to advance the remainder of the device. Hence, inversion is effected at a location selected by the user, independent of patient anatomy or geometric interference. One embodiment of the invention achieves this precise positioning through attachment to a distal end of the device.

Two aspects of the present invention provide reliable performance of the delivery device of the present invention. A first aspect is an attachment mechanism that can be mounted to a braided device without requiring significant modification to the function of the braided device. This attachment mechanism provides device stabilization during the support structure inversion process. This attachment mechanism provides both attachment to the device and a release capability in some embodiments. A second aspect of the present invention includes positioning mechanisms that prevent movement of the device in the target location during the inversion process.

Another aspect of the present invention provides freedom of motion to the support structure anchors as the device is being deployed, but automatically actuates anchor locking mechanisms when the device has been advanced to the appropriate position for the inversion process. This automatic actuation reduces the need for physician involvement or judgment in the tensioning and setting of the anchor mechanisms. The nature of the mechanism also accounts for manufacturing and use tolerances, precisely tuning the anchor locking mechanism to the selected valve and delivery system.

Yet another aspect of the invention provides a deployment device that allows the positioning, implantation and deployment of a prosthetic valve such that the valve achieves complete function prior to releasing the valve. The valve may be observed and verified that it is functioning normally prior to release. If the valve is not functioning as intended, the entire device may be quickly pulled back into the delivery device. In some circumstances, the valve is able to be relocated and redeployed.

Still another aspect of the invention provides a delivery device that includes a limiter that may be set prior to or during the procedure. The limiter ensures that the braided implant does not exit the delivery device more than a desired amount, prior to inverting.

BRIEF DESCRIPTION OF THE DRAWINGS

FIG. 2b is a perspective view of a distal end of an alternative embodiment to that of FIG. 2a;

DETAILED DESCRIPTION OF THE INVENTION

Figure 1:
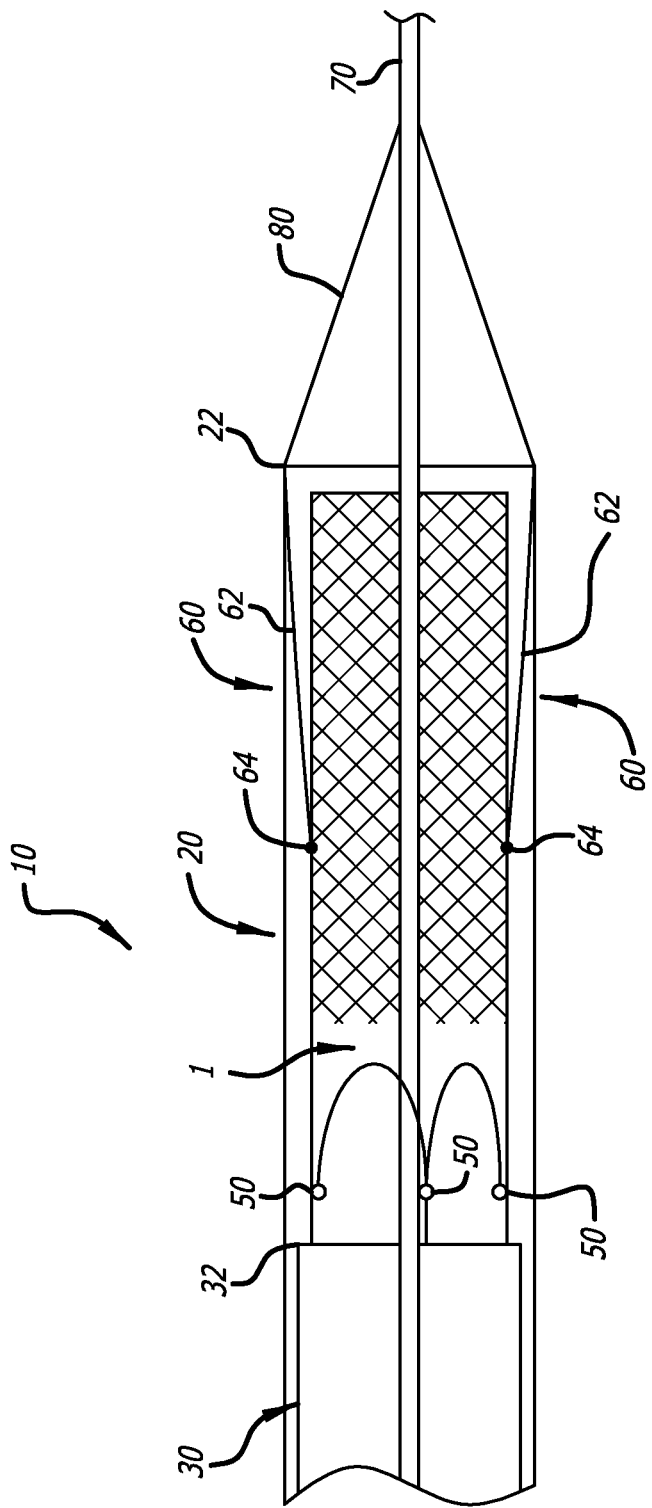
FIG. 1 is a partial cross-sectional view of an embodiment of a delivery device of the present invention with an implant loaded in a distal end thereof.

Referring now to the Figures and first to FIG. 1, there is shown a distal end of a delivery device 10 of the present invention. The delivery device generally includes a delivery catheter 20, and a pusher catheter 30 slidably contained within the delivery catheter 20. The pusher catheter 30 is preferably a multi-lumen catheter containing lumens for slidably containing and maintaining alignment of three attachment cables 40 (hereinafter "valve retention cables") (see FIG. 3), each of which has a releasable grasping mechanism 50 at a distal end thereof. The delivery device 10 also includes at least one positioning mechanism 60 used to aid the tool or implant 1 in achieving a folded, deployed configuration from an extended, unfolded, navigation configuration. In one embodiment, the at least one positioning mechanism 60 is attached to a distal end of the delivery catheter 20. In another embodiment, the at least one positioning mechanism 60 is slidably contained within the delivery catheter 20, similar to the valve retention cables 40.

The delivery catheter 20 is an external sheath defining a single lumen for housing the pusher catheter 30, the tool or implant 1, the valve retention cables 40, and the positioning mechanisms 60. The delivery catheter 20, when loaded, houses a tool or implant 1 near its distal end 22. The implant 1 is preferably an implant similar to those taught and described in U.S. Patent Publication No. 2006/0271166. The delivery catheter 20 may be formed with a preset curve at its distal end. Positive results have been achieved with a 180 degree preset curve.

The pusher catheter 30 may include up to seven lumens. Three lumens slidably house the three valve retention cables 40. In an embodiment used over-the-wire, a fourth lumen accommodates a guidewire. In yet another embodiment, three additional lumens slidably house three positioning mechanisms, described below.

Figure 2A:
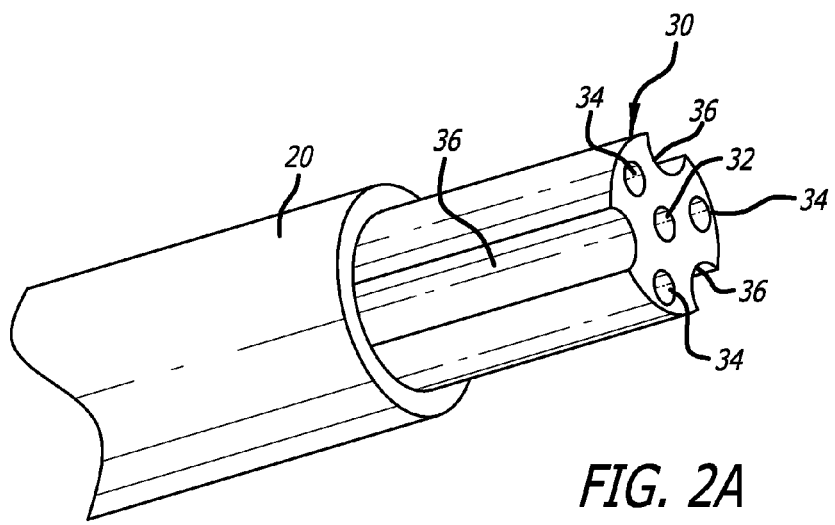
FIG. 2a is a perspective view of a distal end of an embodiment of a pusher catheter of the present invention.
Figure 2B:
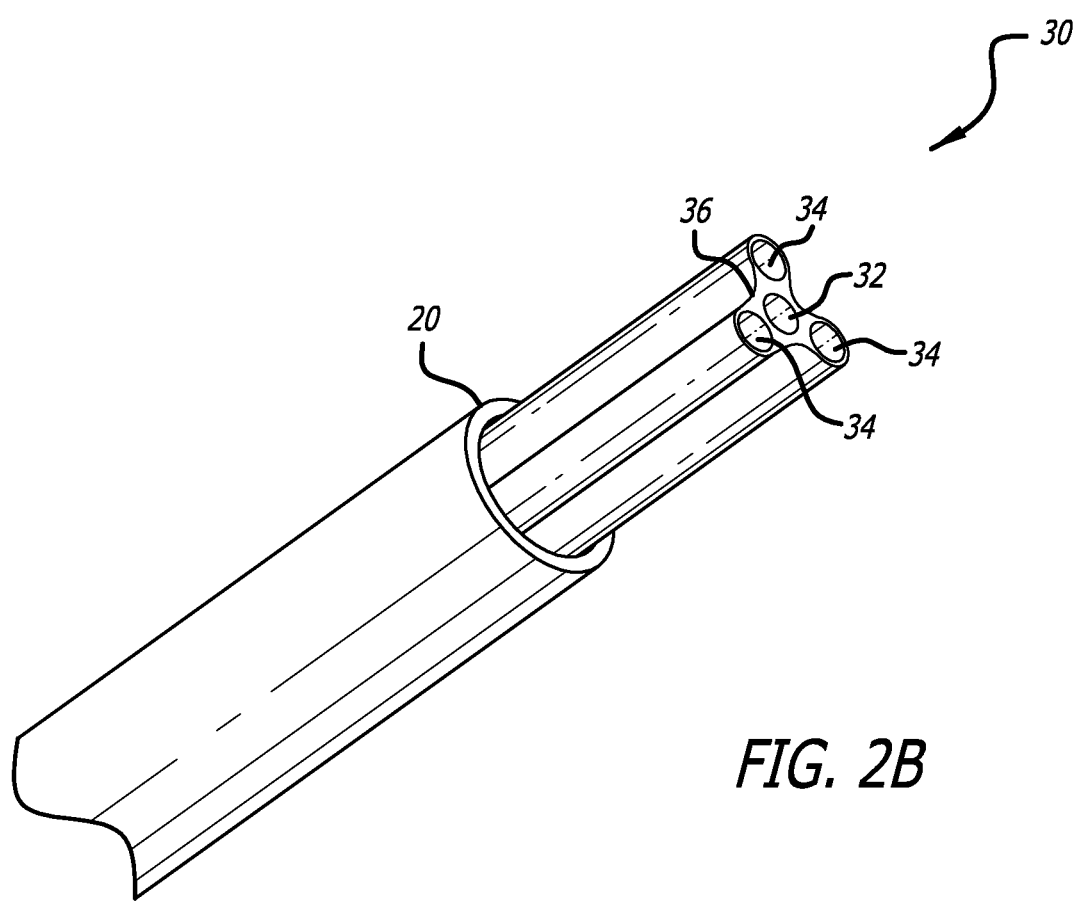

FIGS. 2a and 2b show two similar embodiments of the pusher catheter 30 of the present invention defining seven lumens. The pusher catheter 30 includes a central guidewire lumen 32, and three lumens 34 that contain either the valve retention cables 40 or the positioning mechanisms described below. The remaining three lumens 36 house the remaining valve retention cables or positioning mechanisms. In order to save on space, the lumens 36 may be formed as external indentations, thereby relying on the inner wall of the delivery catheter 20 to complete the lumen and contain the remaining valve retention cables or positioning mechanisms. In a preferred embodiment, the lumens 34 contain the valve retention cables 40 and the lumens 36 contain the positioning mechanisms 60. In this embodiment, the pusher catheter 30 may continue to be advanced even if the positioning mechanisms 60 can no longer be advanced.

In one embodiment, the positioning mechanisms are small enough to fit three valve retention mechanisms, and an associated containment sheath, in a single lumen 36, leaving two other lumens 36 unused or available for use as irrigation channels.

Figure 3:
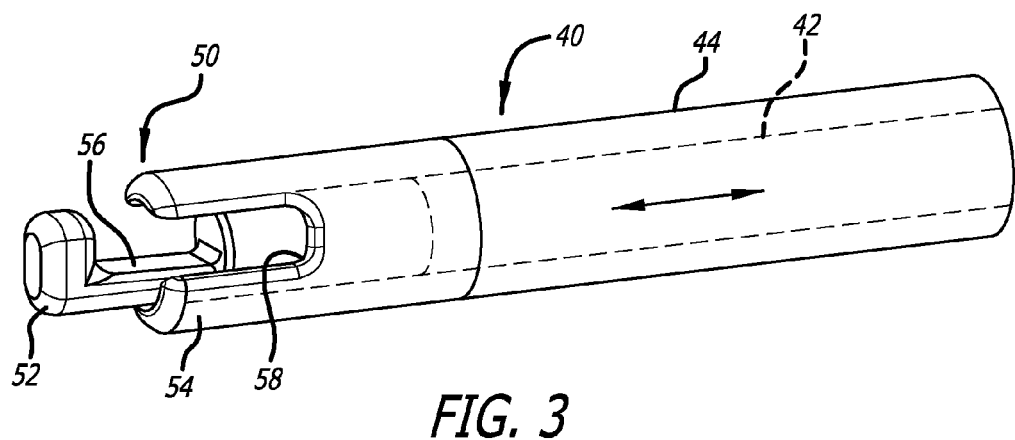
FIG. 3 is a perspective view of an embodiment of a distal end of a release mechanism of the present invention in an open configuration.
Figure 4:
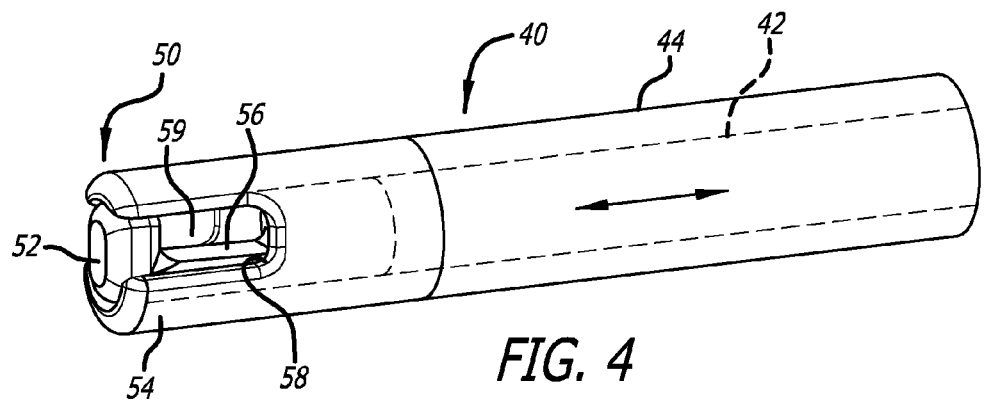
FIG. 4 is a perspective view of the mechanism of FIG. 3 in a closed configuration.

The releasable grasping mechanisms 50 may be similar to those shown and described in U.S. Pat. Pub. 2008/0082165 (at FIGS. 5-8). Another embodiment of releasable grasping mechanisms is shown in FIGS. 3 and 4. The grasping mechanisms 50 are attached to commissural points on an implant 1 when the device 10 is loaded. The grasping mechanism 50 provide the ability to retract the implant back into the device 10 in the event that the physician feels doing so is appropriate.

FIG. 3 shows a grasping mechanism 50 in an open configuration. The grasping mechanism 50 includes a hook 52 that slides within a mouth 54. The hook 52 defines a recess 56 sized to accommodate a component, such as a commissural point or a braid, of the tool or implant 1. The mouth 54 defines a slot 58 that is also sized to accommodate the component. FIG. 4 shows that when the grasping mechanism 50 is in a closed configuration, the recess 56 and the slot 58 together define a passage 59 that traps the component therein.

The grasping mechanism 50 is attached to a distal end of an valve retention cable 40. The valve retention cable 40 includes a wire 42 attached to the hook 52 and an elastomeric sheath 44 that is attached to the mouth 54. The wire 42 and the hook 52 are slidably contained within the sheath 44 and the mouth 54. The sheath 44 is elastomeric such that it is capable of being compressed longitudinally. This feature prevents accidental release of a tool or component contained within the passage 59. For example, when pulling a tool or implant back into the delivery sheath 20 during a retrieval, a load is placed on the wire 42, causing the wire to stretch. If the sheath 44 were not compressed, the wire 42 could stretch enough to cause the hook 52 to exit the mouth 54, thereby assuming the open configuration of FIG. 3. However, because the sheath 44 is compressed when the hook 52 is drawn into the mouth 54 during closing, the sheath 44 elongates when the wire 42 is stretched, thereby maintaining the closed configuration of FIG. 4.

The positioning mechanisms 60 aid in inverting the tool or component 1. In one embodiment, shown in FIGS. 1, 5 and 6, the positioning mechanisms 60 connect the delivery catheter 20 with a first inversion pre-fold point (also referred to herein as an "aortic flare") on the implant 1.

The positioning mechanisms 60 may comprise a plurality of tethers 62 and connectors 64. The tethers 62 may be any resilient strand-like material, flexible enough to invert from a navigation configuration to a deployment configuration. In the navigation configuration, as shown in FIG. 1, the tethers extend proximally from the distal end of the delivery catheter 20, to the connectors 64. In the deployment configuration, shown in FIGS. 5 and 6, the tethers 62 extend distally from the distal end of the delivery catheter 20 to the connectors 64. In one embodiment, the connectors 64 are able to grasp any individual braid or strand of an implant 1. In another embodiment, the connectors 64 are designed to grasp the intersection of two braids or strands. In yet another embodiment, the connectors 64 are able to grasp discrete attachment points (e.g. wire loops, sutures, etc.), that have been integrated into the mesh implant or tool 1. The length of the tethers 62 are at least the length of the material of the implant 1 that extends distally of the connectors 64 when the implant 1 is loaded into the delivery catheter 20. This way, the implant 1 remains completely within the delivery catheter 20 in the navigation configuration.

In another embodiment, the positioning mechanisms 60 are similar in construction to the valve retention cables 40 and releasable grasping mechanism 50. However, because the strength requirements of the positioning mechanisms 60 are less than those of the valve retention cables 40 and their releasable grasping mechanisms 50, the positioning mechanisms 60 may be smaller in diameter, thereby allowing a smaller overall delivery device 10. Rather than being attached to the distal end of the delivery catheter 20, as described above, the positioning mechanisms 60 of this embodiment are slidably contained within the lumens 36 of the pusher catheter 30 shown in FIG. 2.

Figure 5:
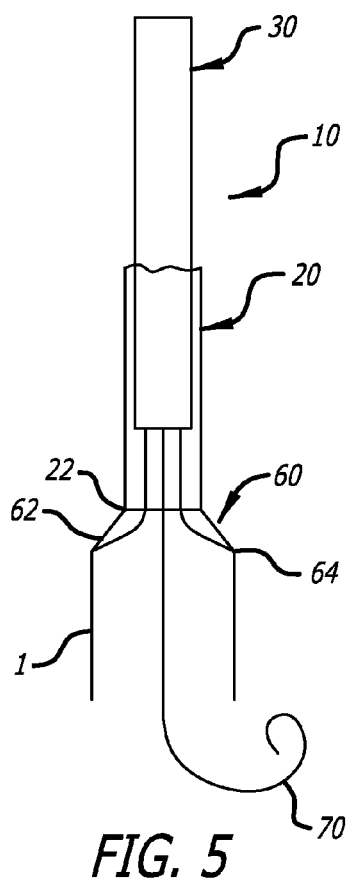
FIG. 5 is a plan cross-sectional view of an embodiment of a delivery device of the present invention, just prior to an inversion process of an implant.
Figure 6:
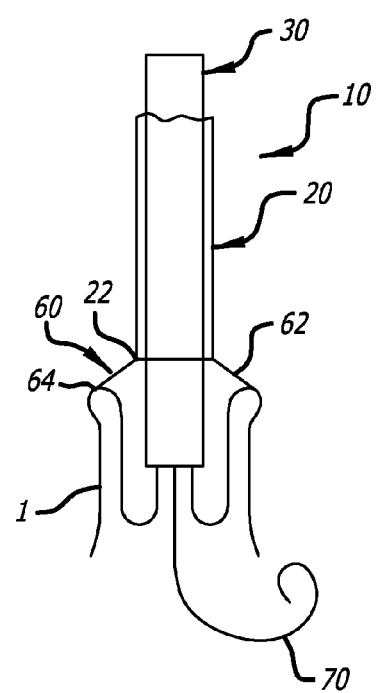
FIG. 6 is a plan cross-sectional view of an embodiment of a delivery device as shown in FIG. 1, just after the implant has been inverted.

Referring to FIGS. 5 and 6, the device 10 is designed to be able to pass over a guidewire 70 during navigation. A conical or otherwise tapered dilator tip 80 abuts against the distal end 22 of the delivery catheter 20 and is flush therewith. The dilator 80 allows the device 10 to be passed through the vasculature with minimal trauma. The dilator 80 is not physically attached to the delivery catheter 20, such that it is easily moved distally during delivery of the implant 1 to avoid interference with the deployment of the implant 1.

Having described the various components of the present invention, the various steps and configurations that occur during navigation and deployment of an implant can now be explained. FIG. 1 shows the navigation configuration of the device 10. In the navigation configuration, the implant 1 is loaded into the distal end of the delivery catheter 20 such that the implant 1 is in an elongated, non-folded state. The pusher catheter 30 is positioned within the delivery catheter 20 with its distal end 22 proximal of the implant 1. The valve retention cables 40 extend distally from the pusher catheter 30 and are connected to commissural points of the implant 1 with the releasable grasping mechanisms 50. The conical dilator 80 abuts against the distal end 22 of the delivery catheter 20. During navigation, the entire device 10 and implant 1 travel over a guidewire 70 to the target location.

FIG. 5 shows the initial stages of deployment of the implant 1. The target location has been reached and the delivery catheter 20 is retracted while the pusher catheter 30 and valve retention cables (40) remain stationary relative to the target location. Retracting the delivery catheter 20 causes the pusher catheter 30 to push the implant 1 out of the distal end 22 of the delivery catheter. As the implant 1 exits the delivery catheter 20 the implant 1 expands and the positioning mechanisms 60 are advanced through the delivery catheter 20 until the tethers 62 become taut, or in the case of the positioning mechanisms that are slidably contained within the lumens of the pusher catheter 30, the positioning mechanisms 60 can no longer be advanced.

As seen in FIG. 6, further advancement of the pusher catheter 30 causes implant material that is proximal of the connectors 64 to invert into the implant material that is distal of the connector 64. This is because the positioning mechanisms 60 are taut and do not allow further distal advancement of the implant 1. As such, the inversion of the implant 1 is urged by the preformed fold in the implant, the expansion of the memory metal making up the implant 1, and the restraint provided by the positioning mechanisms 60. Notably, the transition of the implant from initial advancement to inversion happens automatically and is dictated by the length of the tethers 64. As such, operator experience is not required to initiate inversion. Nor is there any reliance on anatomical structure to provide friction against the implant to initiate inversion.

Once the implant 1 has been fully deployed, the implant 1 is fully functional prior to release. This allows verification of proper operation of the implant 1 via one or more imaging modalities prior to full release of the implant 1. If proper operation is not achieved, the grasping mechanisms 50 can be used to pull the implant 1 back into the delivery catheter 20 such that the implant may be either removed or redeployed. If proper operation is verified, the connectors 64 are actuated to release the braids or strands of the implant 1. The pusher catheter 30 and the delivery catheter 20 are withdrawn slightly while maintaining connection with the implant 1 and the device 10 via the releasable grasping mechanism. Subsequently, the grasping mechanisms 50 are actuated to release the commissural points of the implant 1. The pusher catheter 30 is retracted into the delivery catheter 20 and the delivery catheter 20 and the guidewire 70 are withdrawn from the patient.

FIGS. 7-21 illustrate another embodiment of a delivery device 100 that is generally similar to the previously described delivery device 10, especially where noted with similar element numbers. However, the delivery device 100 includes a positioning tether assembly 110, the distal end of which is seen best in FIGS. 7-10, having a sliding release mechanism for releasing a connection to the implant 1.

More specifically, the positioning tether assembly 110 includes a plurality of tethers 104 that are each arranged in a generally closed loop. These looped tethers 104 pass through portions of the implant 1 and therefore can maintain the implant 1 in a desired position during a procedure (e.g., can prevent distal movement of the implant 1). The tethers can be disconnected from the implant 1 by releasing one end of each of the tethers 104, effectively opening the loop shape. In this respect, withdrawal of the positioning tether assembly 110 also pulls the tethers 104 out of and away from the implant 1.

Figure 7:
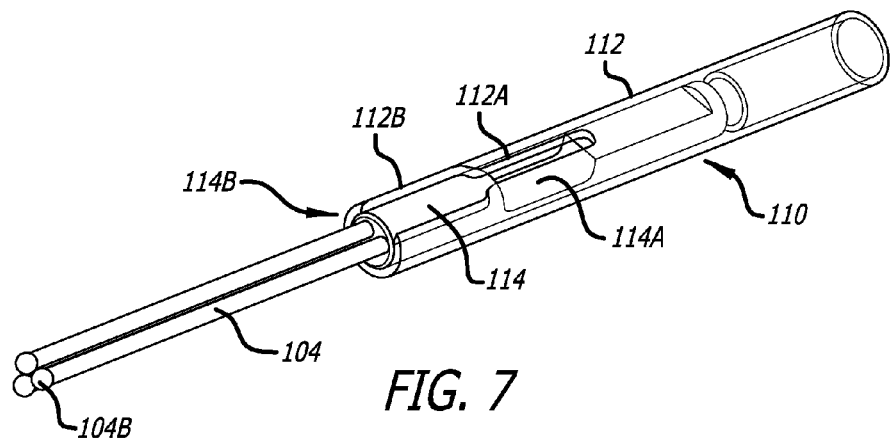
FIG. 7-10 are perspective views of a pusher catheter of an embodiment of a delivery device.
Figure 8:
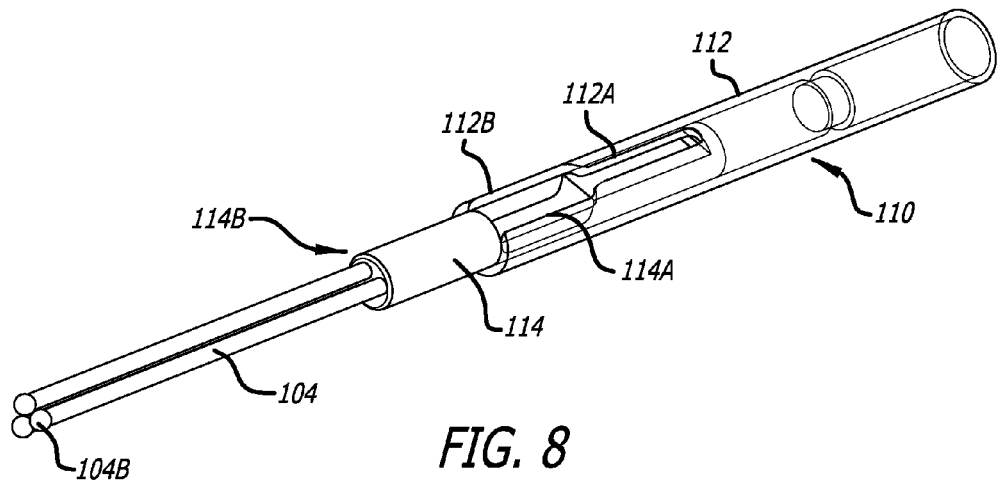
Figure 9:
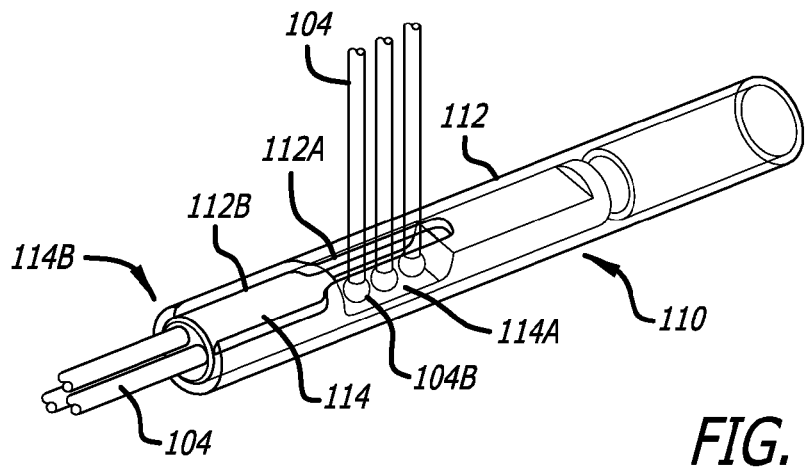
Figure 10:
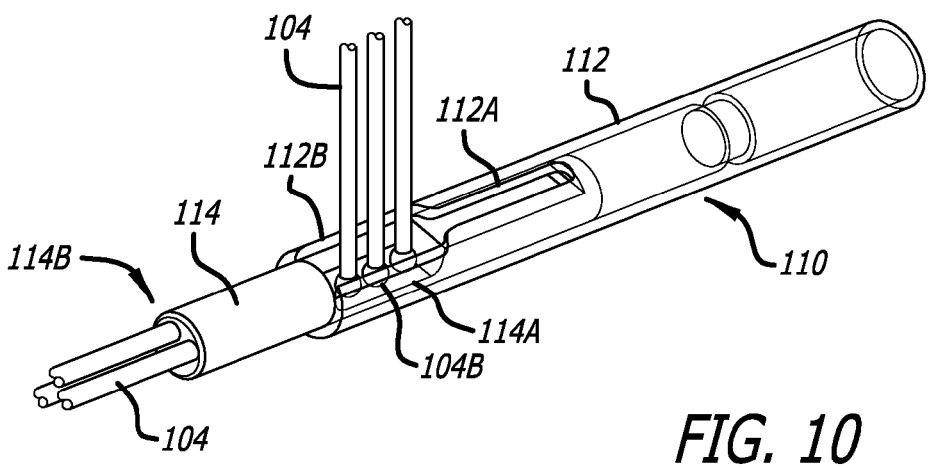
Figure 11:
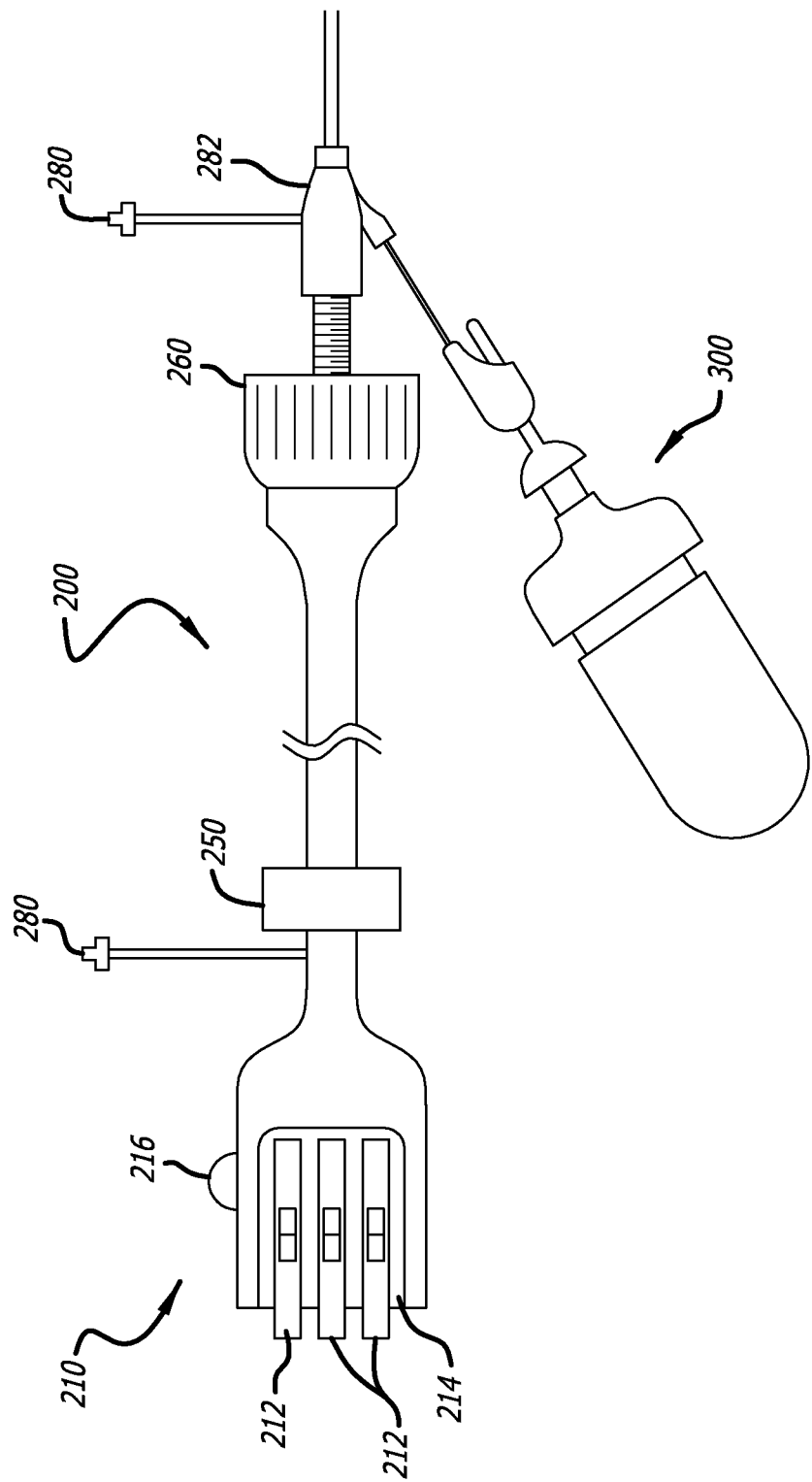
FIG. 11 is a plan view of an embodiment of a handle assembly of the invention.

The release mechanism of the positioning tether assembly 110 is triggered by advancing a sliding member 114 to the position seen in FIGS. 8 and 10 from the retracted position seen in FIGS. 7 and 9. Note that the tethers 104 are connected to a distal end 114B of the sliding member 114 (e.g., either fixed in place or pass through the member 114 back to the proximal end of the positioning tether assembly 110), but for illustrative purposes are not shown as such in FIGS. 9 and 10. Initially, the free ends 104B of the tethers 104 are located within a depression 114A of the sliding member 114 and are captured by a first slot 112A of an outer tether sheath 112. When the sliding member 114 is advanced, the depression 114A is positioned beneath a wider, second slot 112B, which allows the free ends 104B of the tethers 104 to be released.

As best seen in FIG. 9, the free ends 104B of the tethers 104 have a generally larger size or diameter than the remaining portion of the tether 104 and can have a variety of different shapes, such as rounded, spherical or even square. The first slot 112A has a width that is large enough to accommodate the diameter of the tether 104 but is smaller than the diameter of the free ends 104B, thereby allowing the tether 104 to laterally slide within the slot 112A without the free ends 104B from traversing through.

The second slot 112B is positioned distal to the first slot 112A and has a width that is larger than the free ends 104B. In this respect, once the depression 114A aligns under this second slot 112B, as seen in FIG. 10, the free ends 104B are released, thereby allowing the tethers 104 to assume a generally linear configuration, similar to that in FIG. 8.

While two slots are shown, a single slot may alternately be used in another embodiment. Specifically, the single slot may be similar in size to slot 112A, but extends to the distal end of the tether sheath 112. In this respect, the free ends 104B are released when the depression 114A is advanced outside of the tether sheath 112.

The positioning tether assembly 110 may be constructed with an overall outside diameter that is small enough to be slidingly contained in one of the lumens 34 or 36 of the pusher catheter 30 shown in FIG. 2a or 2b.

FIGS. 11-22 show the proximal end or handle assembly 200 of the delivery device 100. The handle assembly generally includes valve retention cable control group 210, a pusher catheter control 250, a drive mechanism 260, irrigation ports 280, and a tether control assembly 300.

The valve retention cable control group 210 includes a plurality of valve retention cable controls 212, housed in a recess 214 of the handle 200, and a locking pin 216. The individual valve retention cable controls 212 are best seen in FIGS. 12-14.

Figure 12:
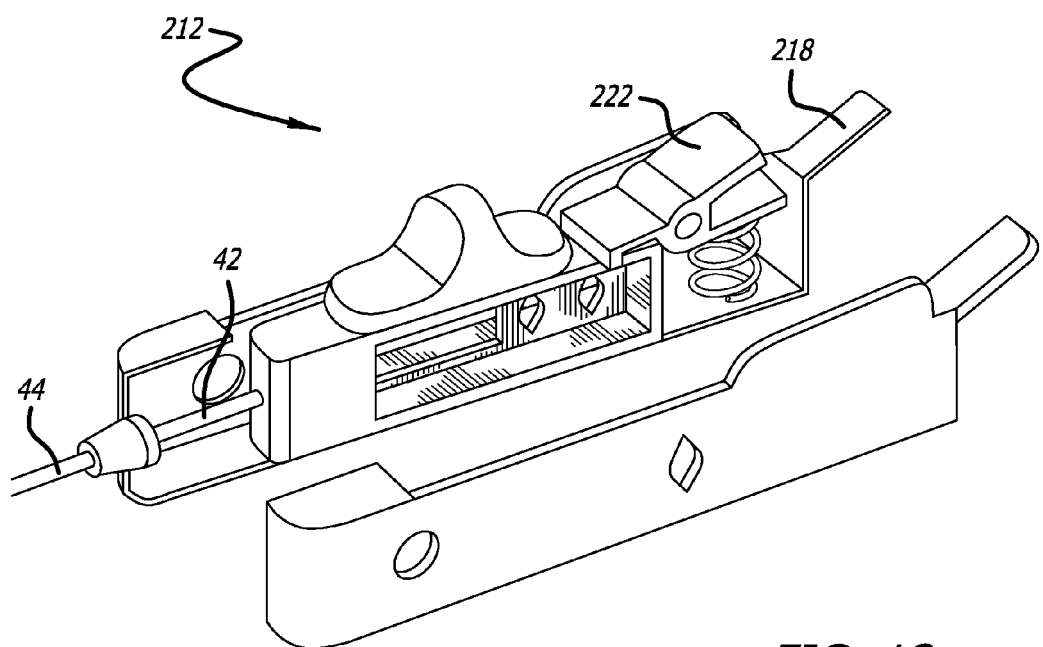
FIG. 12 is an exploded view of an embodiment of a valve retention cable control of the invention.
Figure 13:
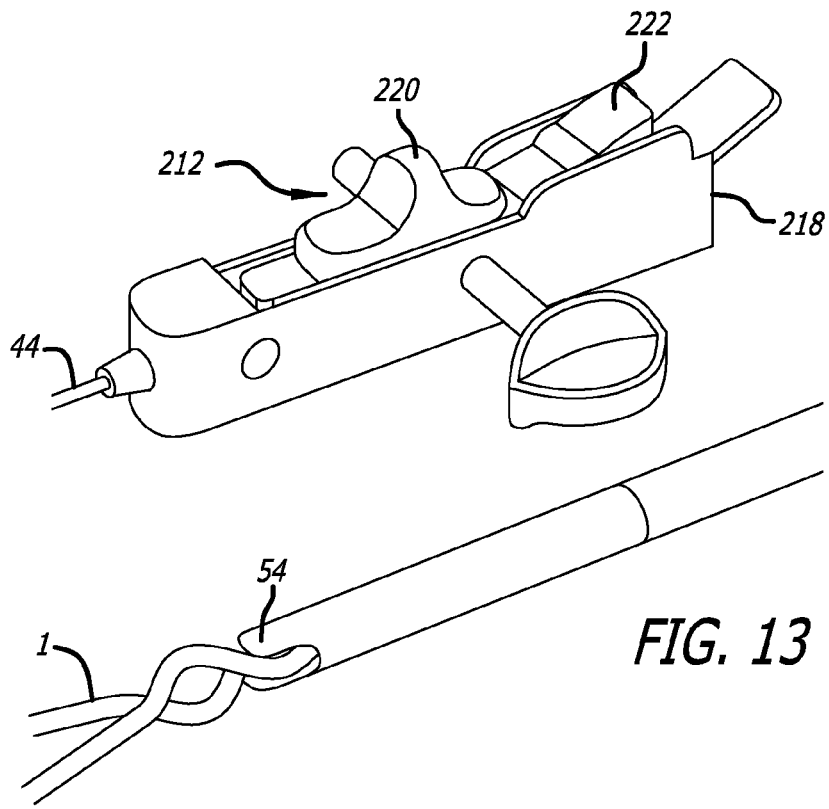
FIG. 13 is a perspective view of an embodiment of a valve retention cable control of the invention in a closed position.

FIG. 12 shows an exploded view of an individual valve retention cable control 212. The control 212 includes a housing 218, to which is attached a proximal end of the elastomeric sheath 44 of the retention cable 40 (see FIG. 3). Slidingly contained within the housing 218 is a thumb slide 220, which is connected to the wire 42 of the retention cable 40. Behind the thumb slide 220 is a spring-loaded catch 222. In operation, pulling the thumb slide rearward toward the catch 222 pulls the wire 42 relative to the sheath 44, thereby retracting the hook 52 into the mouth 54 at the distal end of the cable 40. The catch 222 maintains the retention cable 40 in a closed position. The hook 52 can be quickly released from the mouth 54 by depressing the catch 222.

Figure 14:
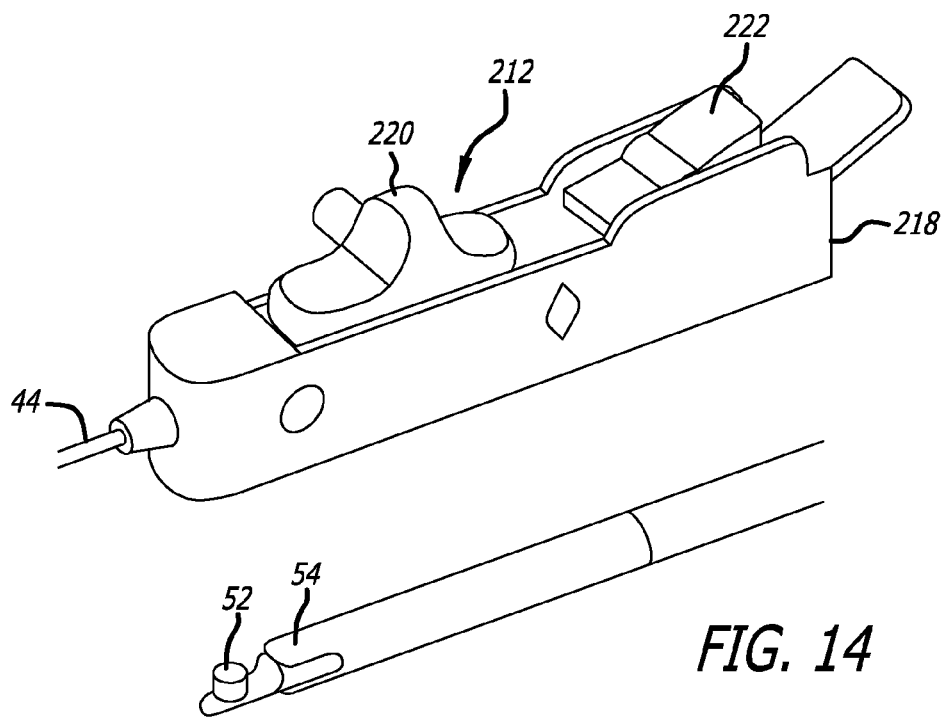
FIG. 14 is a perspective view of an embodiment of a valve retention cable control of the invention in an open position.
Figure 15:
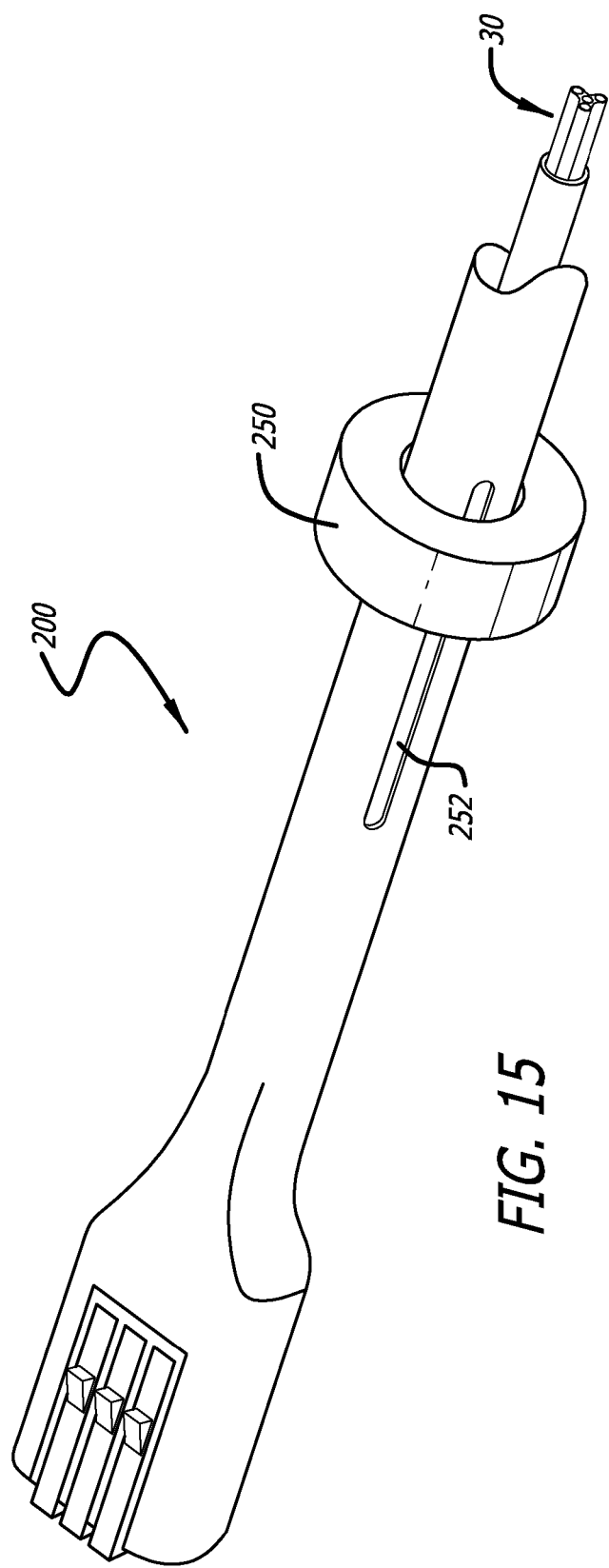
FIG. 15 is a partial perspective view of an embodiment of a handle assembly of the invention showing an embodiment of a pusher catheter control.

FIG. 14 shows the thumb slide 220 in the forward, open position. The corresponding open position of the distal end of the cable 40 is also shown. FIG. 15 shows the thumb slide 220 in the rearward, closed position. The corresponding closed position of the distal end of the cable 40 is also shown. Furthermore, a locking pin 216 has been inserted through the housing 218 and the thumb slide 220 to prevent accidental release of the implant 1 held in the mouth 54 of the retention cable 40.

Referring back to FIG. 11, it is shown that there are three controls 212 arranged in the handle 200. It can also be seen that a single locking pin 216 passes through the handle 200 and all three controls 212. This locking pin 216 is a precautionary feature that ensures none of the controls 212 are inadvertently opened. Once the valve position and operation have been verified, the physician is then able to unlock all three controls 212 by removing the single pin 216.

FIG. 15 is a partial view of the handle 200 of the device 100. FIG. 15 shows the pusher catheter control 250, which is shown as a sliding ring 250 that slides over the handle 200. The ring 250 is connected through a slot 252 in the side of the handle 200 to the pusher catheter 30. When the ring 250 is advanced to its most distal position, it may be rotated to lock the pusher catheter relative to the valve retention cables 40.

Figure 16:
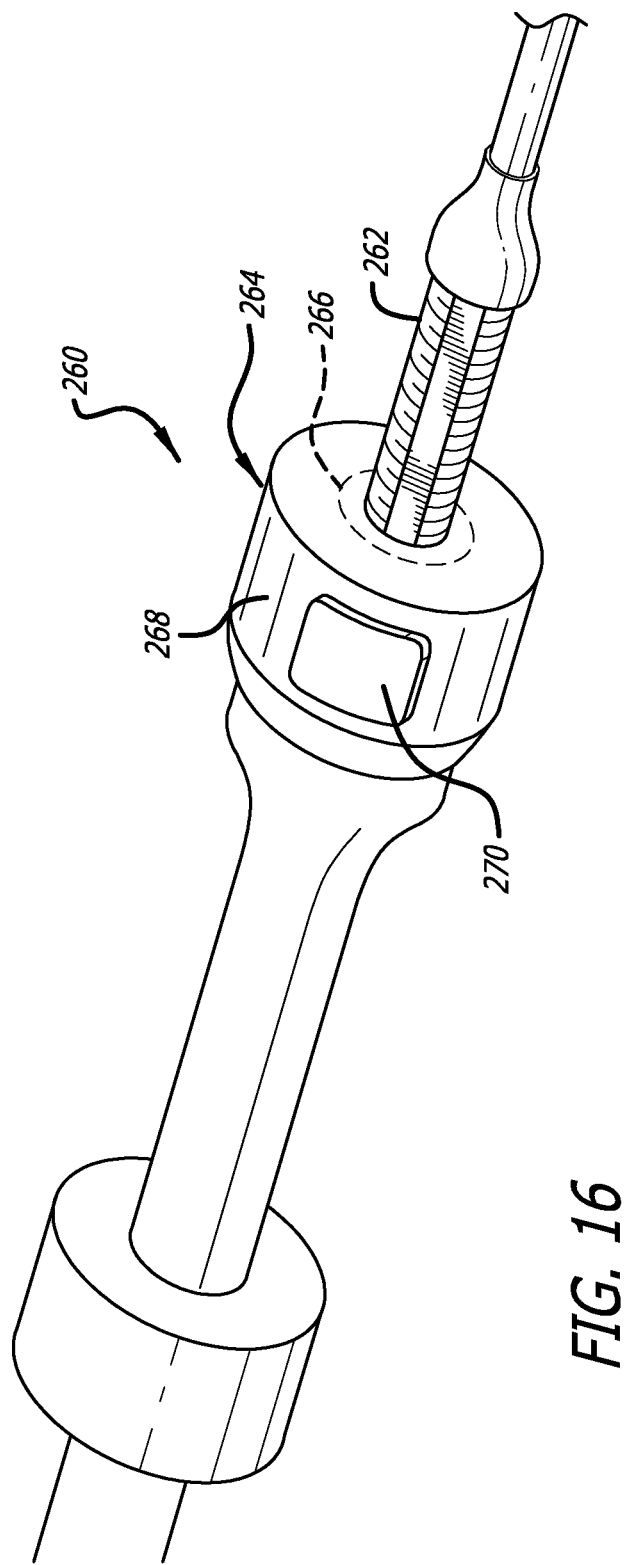
FIG. 16 is a partial perspective view of an embodiment of a handle assembly of the invention showing an embodiment of a drive mechanism.

The drive mechanism 260 is shown in FIG. 16. The drive mechanism 260 includes a lead-screw 262 and a threaded nut combination 264. The threaded nut combination 264 includes a nut 266 contained within a knob 268 and a quick release 270. Rotation of the knob 268 causes the nut 266 to act against the lead-screw 262. The knob 268 is axially fixed relative to the handle 200. The lead-screw 262 is slidingly contained within the handle 200. As such, when the nut 266 acts against the lead-screw 262, the lead-screw 262 advances or retracts in the handle 200. The lead-screw 262 is connected at its distal end to the delivery catheter 20. The rotatable threaded nut combination 264 thus allows precise control over the relative motion between the pusher catheter 30 and the delivery catheter 20. The quick release 270 may be in the form of a button or lever that disengages the nut 266 from the threads of the lead-screw 262 to allow the pusher catheter 30 and valve retention cables 40 to be quickly retracted into the delivery catheter 20.

It has been found that retracting an implant back into the delivery catheter 20 is more successful when done quickly. A slow retraction increases the risk that the catheter may buckle. As such, the handle 200 has been designed to effect a quick retraction of an implant back into the device 100 when necessary. This is accomplished by ensuring the ring 250 is rotated into the locked position so that when the handle is retracted relative to the delivery catheter, the pusher catheter 30 and the valve retention cables 40 are fixed relative to each other and thus retracted simultaneously. Depressing the quick release 270 while pulling on the knob 268 while holding the delivery catheter 20 stable causes the implant to be quickly drawn back into the delivery catheter 20.

The various components of the tether control assembly 300 are shown in FIGS. 17-21. The tether control assembly 300 generally includes a tether release controller 310 and a tether positioning mechanism 340.

Figure 17:
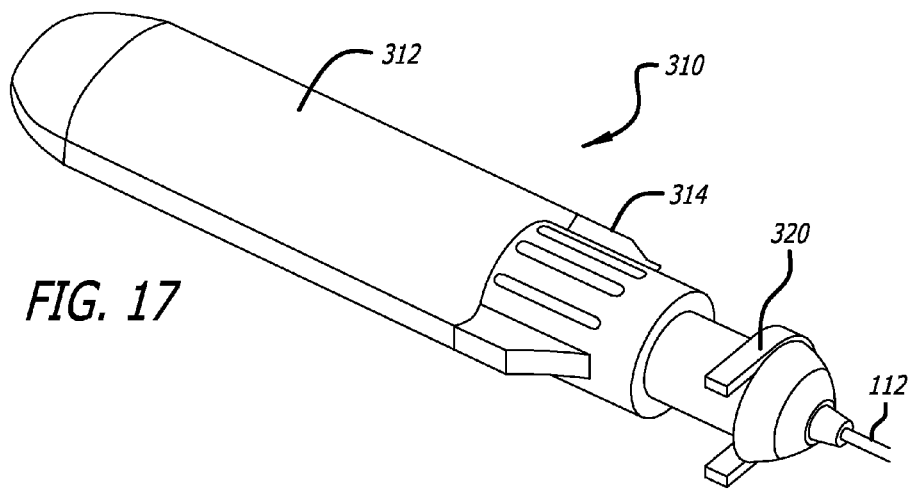
FIG. 17 is a perspective view of an embodiment of a tether release controller of the invention in a closed position.
Figure 18:
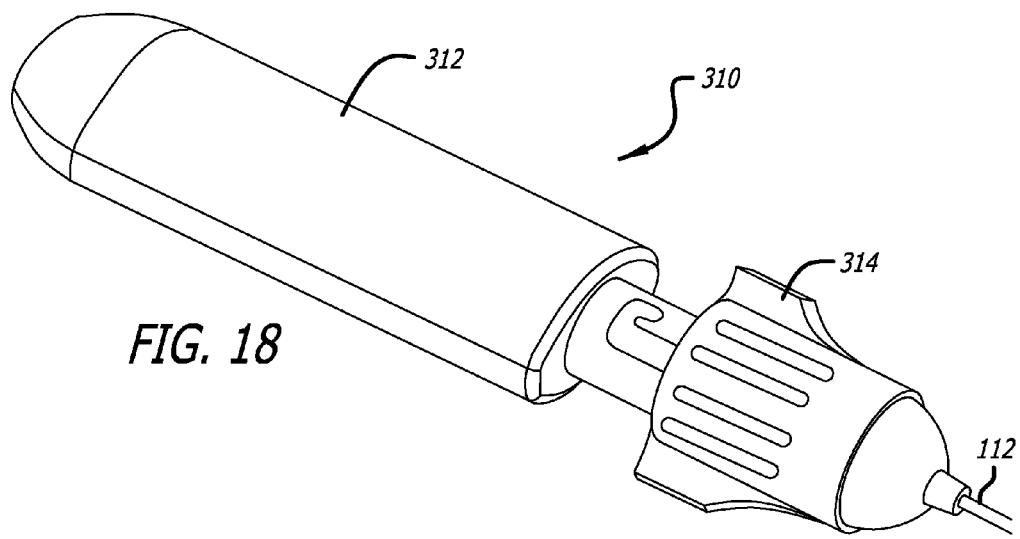
FIG. 18 is a perspective view of an embodiment of a tether release controller of the invention in an open position.

The tether release controller 310 is shown in FIGS. 17 and 18 and includes a housing 312 and a control knob 314. The housing 312 is fixed to the proximal end of the outer tether sheath 112 (See FIGS. 9 and 10) of the positioning tether assembly 110. The control knob 314 is able to slide axially, relative to the housing 312, and is attached to the proximal end of sliding member 114 (FIGS. 9 and 10). Thus, when the control knob 314 is in the forward position shown in FIG. 18, the tethers are released. When the control knob 314 is in the rearward position shown in FIG. 17, the tethers ends are trapped in the first slot 112A of the outer tether sheath 112. In the embodiment shown in the Figures, the control knob 314 can be turned in the closed position, thereby locking it closed. Also includes is a clip 320 which may be used to prevent the control knob 314 from advancing to the open position in the event it is accidentally actuated. The clip 320 is easily removed when it is desired to release the tethers.

Figure 19:
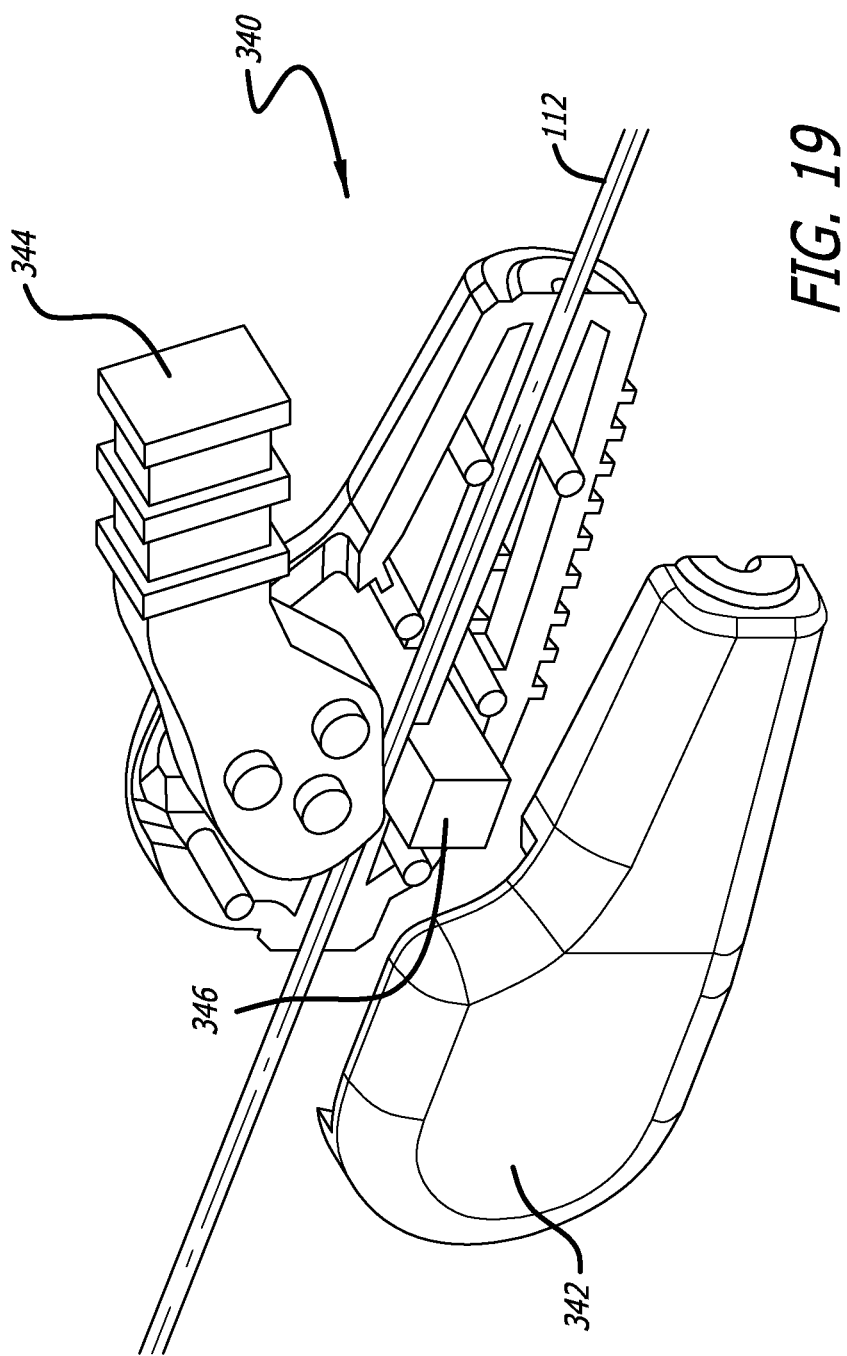
FIG. 19 is an exploded view of an embodiment of a tether positioning mechanism of the invention.
Figure 20:
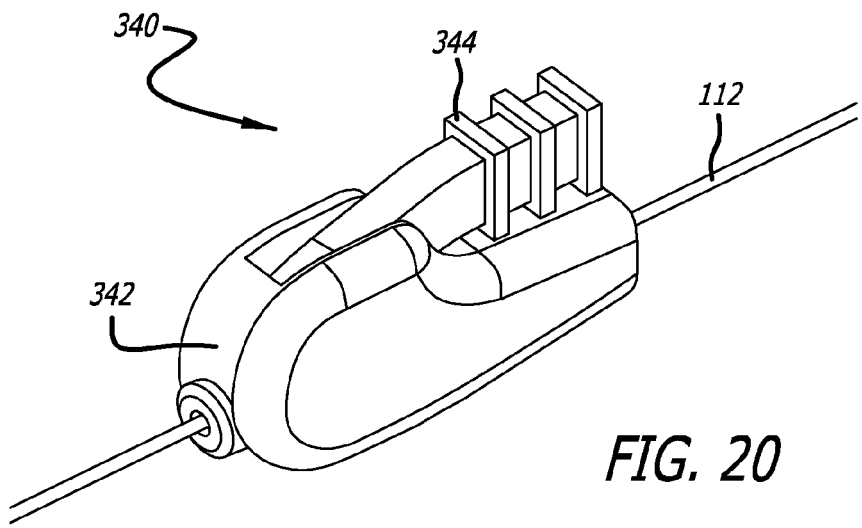
FIG. 20 is a perspective view of an embodiment of a tether positioning mechanism of the invention in a locked position.
Figure 21:
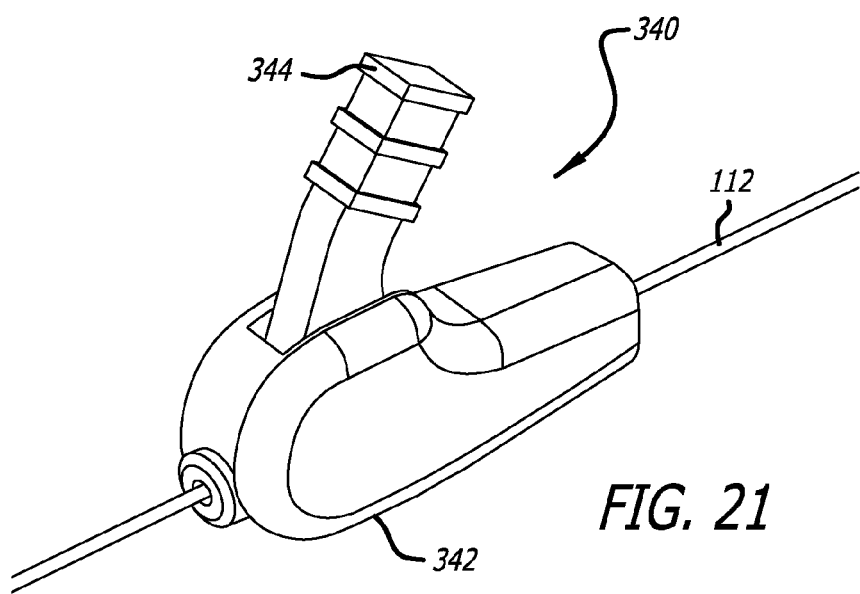
FIG. 21 is a perspective view of an embodiment of a tether positioning mechanism of the invention in an unlocked position.

FIGS. 19-21 show the tether positioning mechanism 340. The tether positioning mechanism is a slide-lock that includes a housing 342, a lever 344, and a clamp block 346. The housing 342 passes over the outer tether sheath 112 and keeps the tether sheath positioned between the lever 344 and the clamp block 346. When the lever 344 is lowered to the closed position, shown in FIG. 20, the outer tether sheath 112, and the tethers contained therein, are clamped between the lever 344 and the block 346, and cannot slide. Thus the tether positioning mechanism 340 is fixed relative to the outer tether sheath 112. When the lever 344 is in the open position, the tether positioning mechanism 340 is able to slide over the outer tether sheath 112.

FIGS. 22-29 illustrate how the delivery device 100 can be used to deliver an implant 1 according to the present invention. First, an implant 1 is loaded into the delivery device 100. After the selected valve is rinsed, each of the three valve retention cables 40 are individually attached to each of three wire form eyelets on the implant. This is accomplished by opening the valve retention cable control 212, pushing the thumb slide 220 forward to expose the hook 52 from the mouth 54. The hook 52 is placed through the wire form eyelet and the thumb slide 220 is retracted rearwardly until it engaged the catch 222. Doing so locks the slide 220 and closes the hook 52 into the mouth 54. It also compresses the outer elastomeric sheath 44 of the valve retention cable 40 to maintain interference between the hook 52 and the mouth 54, even if a pulling force is placed on the cable sufficient to stretch the cable, thereby preventing accidental release during a retrieval procedure.

After all three valve retention cables 40 are attached, the position tethers 104 are attached to the implant 1. (Alternatively, the position tethers 104 may be attached prior to the valve retention cables 40). This is accomplished by threading each of the three tethers 104 through the center of the implant and through a ventricular loop of the implant's support structure at 120 degree intervals from the inside to the outside of the implant. Once all three tethers 104 have been threaded, they are passed back up through the valve and the three tethers 104 are locked within the slot 112A of the outer tether sheath 112. Locking is accomplished by pulling the control knob 314 and rotating it to the locked position shown in FIG. 17.

Next the pusher catheter 30 is pushed forward to capture the valve retention cables 40. At the distal-most position of the pusher catheter control ring 250, the ring 250 is rotated to lock the position of the pusher catheter 30 relative to the valve retention cables 40.

The implant 1 is now ready for loading into the delivery catheter 20. The delivery catheter 20 is advanced by rotating the drive knob 268 toward the user, and the implant 1 is slowly drawn into the distal end of the delivery catheter 20. While the implant 1 is being loaded, the position of the implant is noted so an observation can be made as to when the implant has achieved the orientation in which the implant would be exposed enough from the delivery catheter 20 to be able to invert into itself. At this point the tether positioning mechanism 340, which is in the unlocked position, is slid down the sheath 112 until it contacts the delivery catheter manifold 282 (FIG. 11) and the lever 344 is moved to the locked position.

Continued loading of the implant into the delivery catheter 20 causes the tethers 104 and the tether sheath 112 to retract and the tether positioning mechanism 340 to move proximally relative to the delivery catheter manifold 282. The implant is fully loaded when the dilator tip 80 has been partially retracted into the delivery catheter 20 and there is a smooth transition between the dilator tip and the delivery catheter tip.

Figure 22:
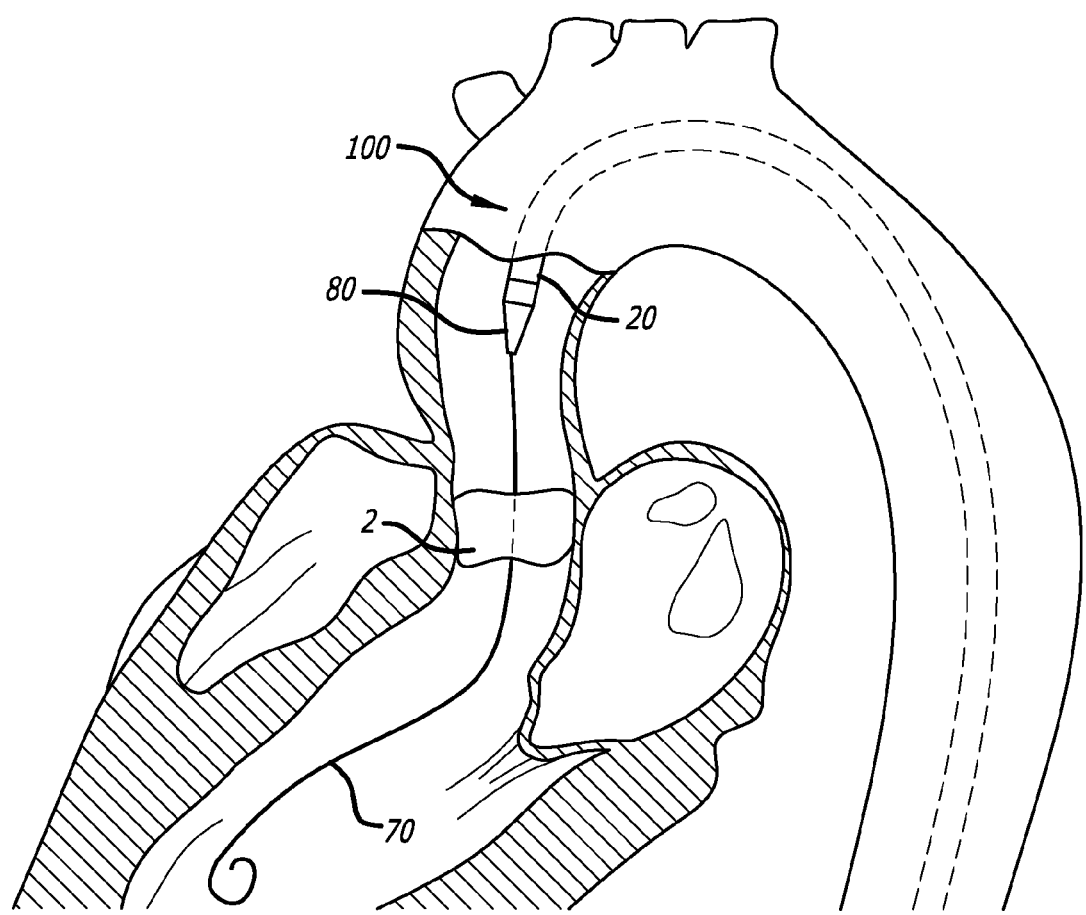
FIG. 22 is a side view of an embodiment of a delivery device of the present invention in a vessel of a patient.
Figure 23:
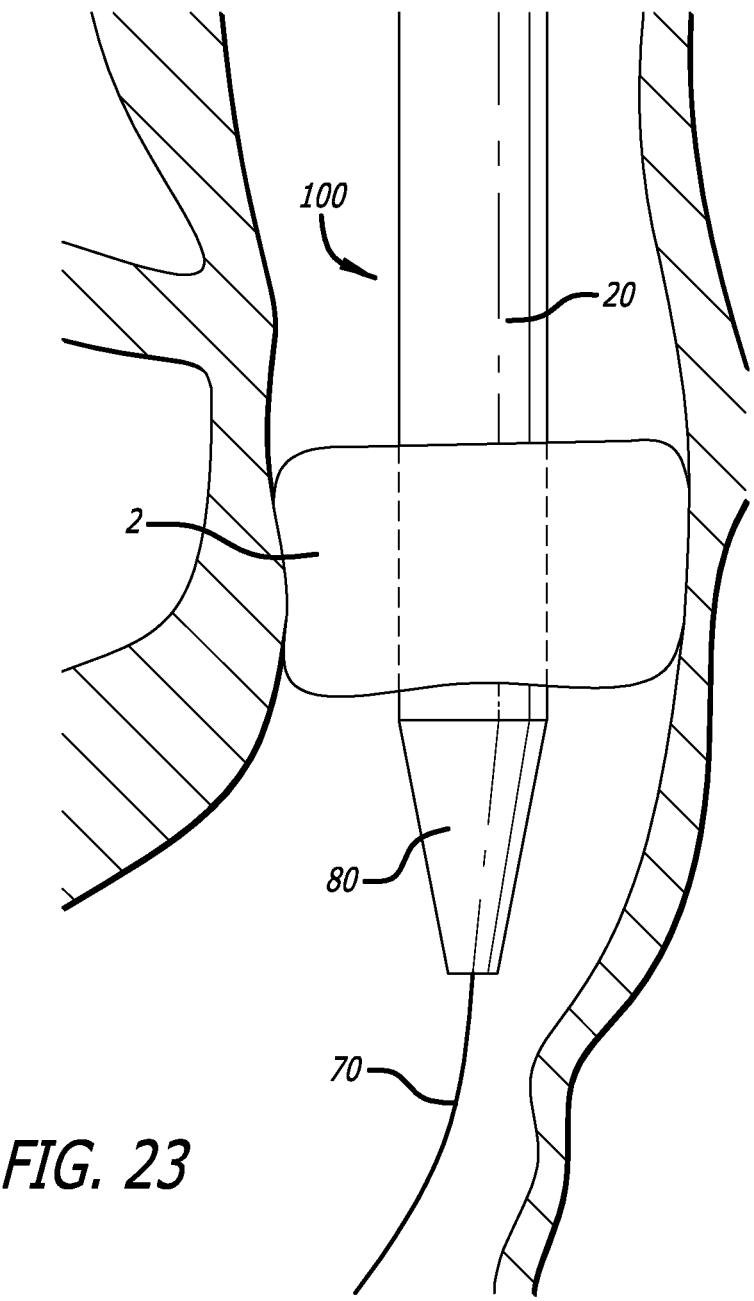
FIG. 23 is a side view of an embodiment of a delivery device as shown in FIG. 22, just after crossing a heart valve.

As seen in FIG. 22, a guidewire 70 is placed across the native aortic valve of the patient and extends out through the vascular introducer at the femoral artery access site. The proximal end of the guidewire is inserted into the dilator tip 80 of the loaded delivery system and the system is advanced over the guidewire until the guidewire is visible through the proximal end of the delivery system. The proximal end of the guidewire is then held stationary in order to maintain the position of the wire in the left ventricle of the patient and the delivery system is advanced into the vasculature through the introducer and across the native aortic valve 4 (seen best in FIG. 23). The guidewire passes through lumen 32 of the pusher catheter 30.

Figure 24:
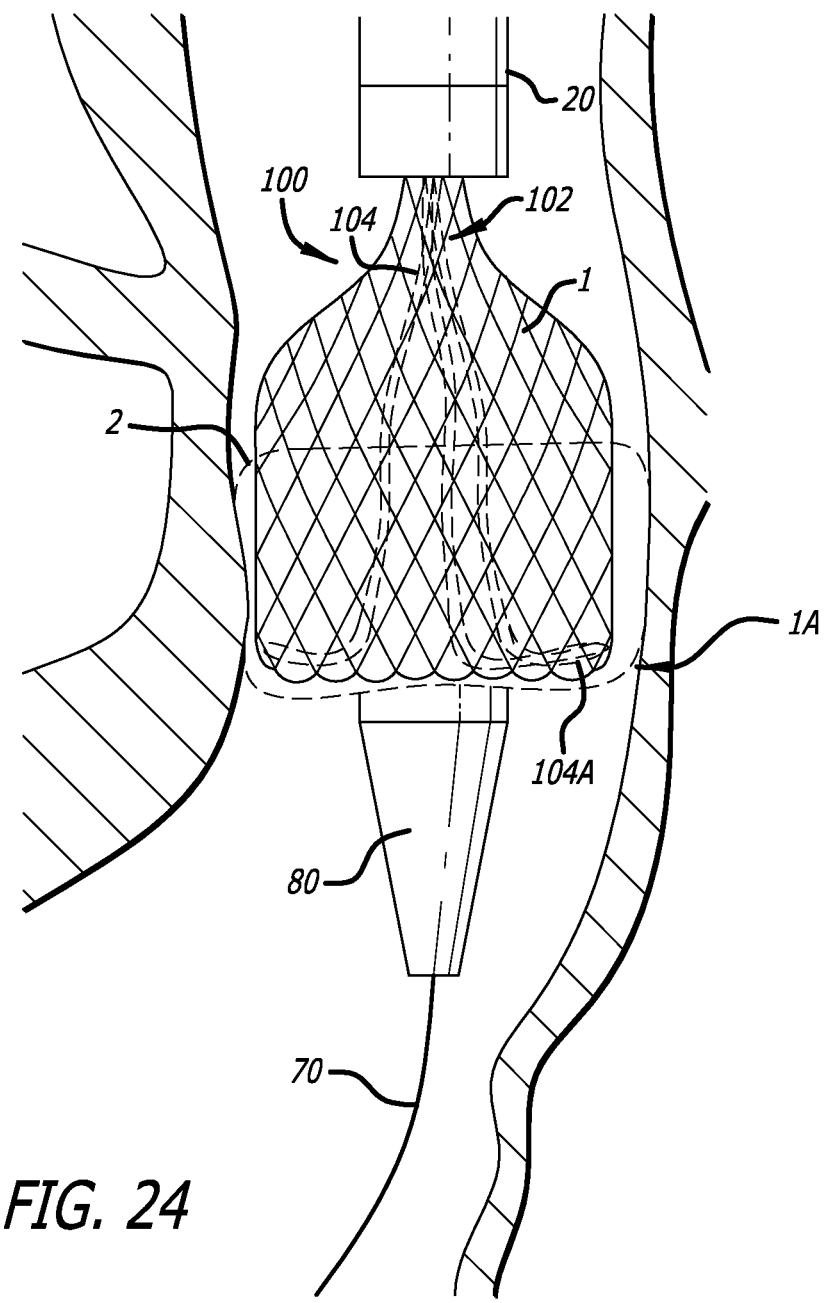
FIG. 24 is a side view of an embodiment of a delivery device as shown in FIG. 22, in which an implant is partially deployed.

Turning to FIG. 24, the delivery sheath 20 is proximally retracted to expose a portion of the implant 1 and the tethers 104. This is accomplished by rotating the drive knob 268. As the implant 1 becomes exposed, it self-expands outward against the native valve 4. During deployment, the operator maintains the implant position within the native valve of the patient. If, however, the implant is pulled too high or pushed too low relative to the native valve, the implant can be recaptured by reversing the direction of the drive knob 268 rotation, which draws the implant back into the sheath 20 for repositioning.

Figure 25:
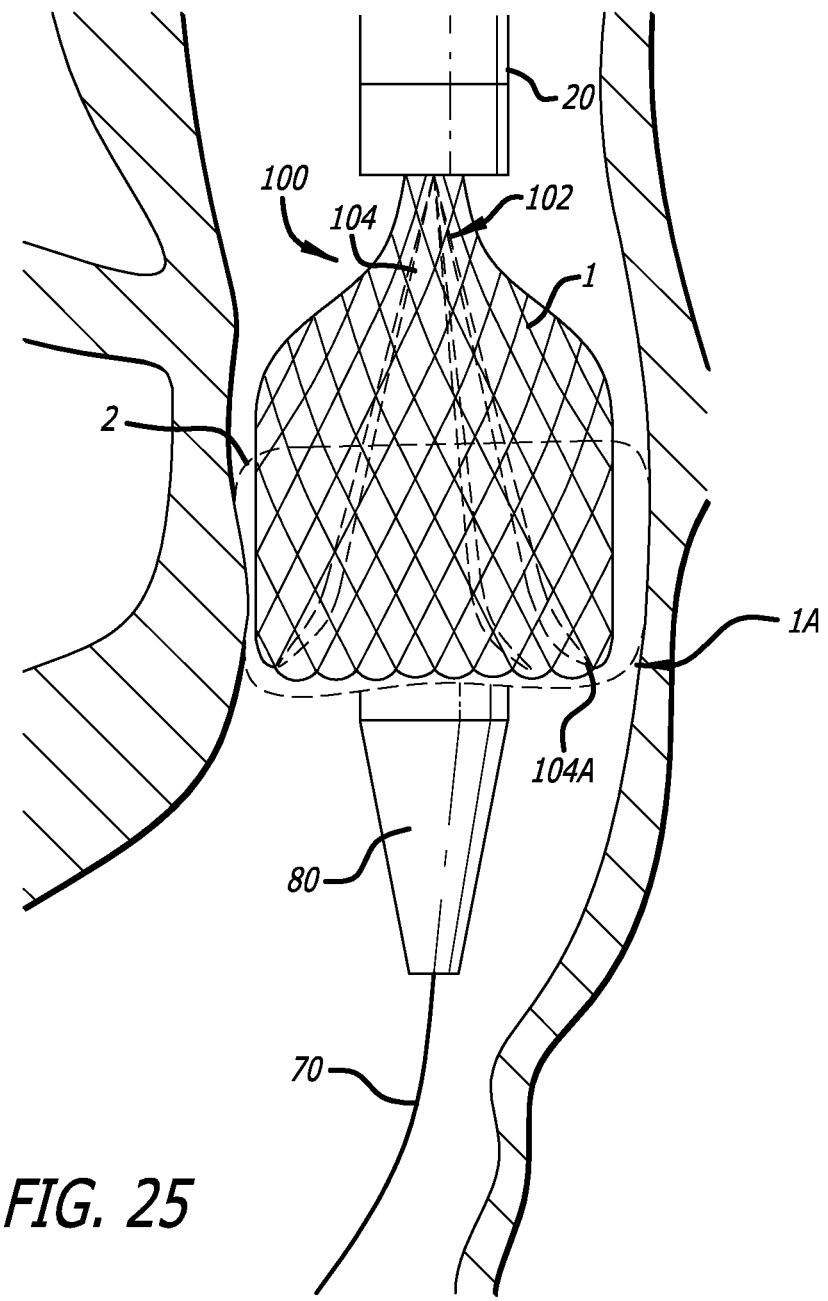
FIG. 25 is a side view of an embodiment of a delivery device as shown in FIG. 22, in which the tethers are tightened.
Figure 26:
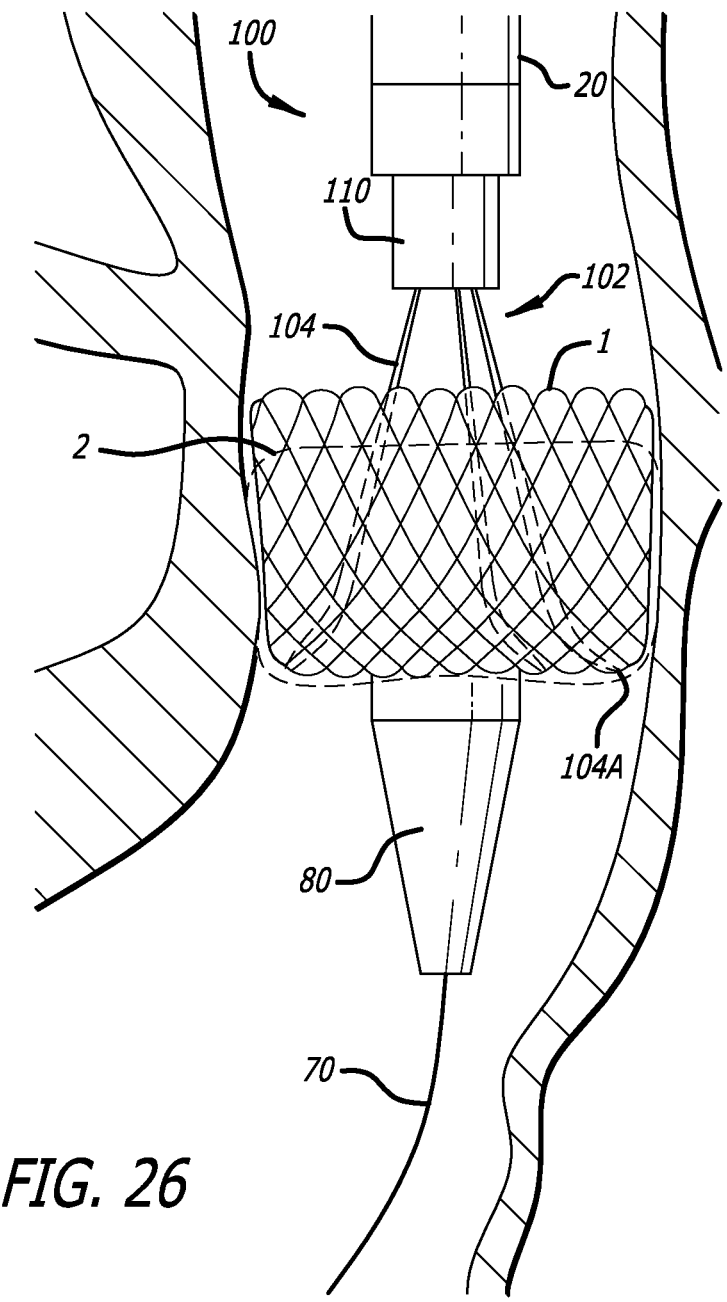
FIG. 26 is a side view of an embodiment of a delivery device as shown in FIG. 22, just after the implant has been inverted.
Figure 27:
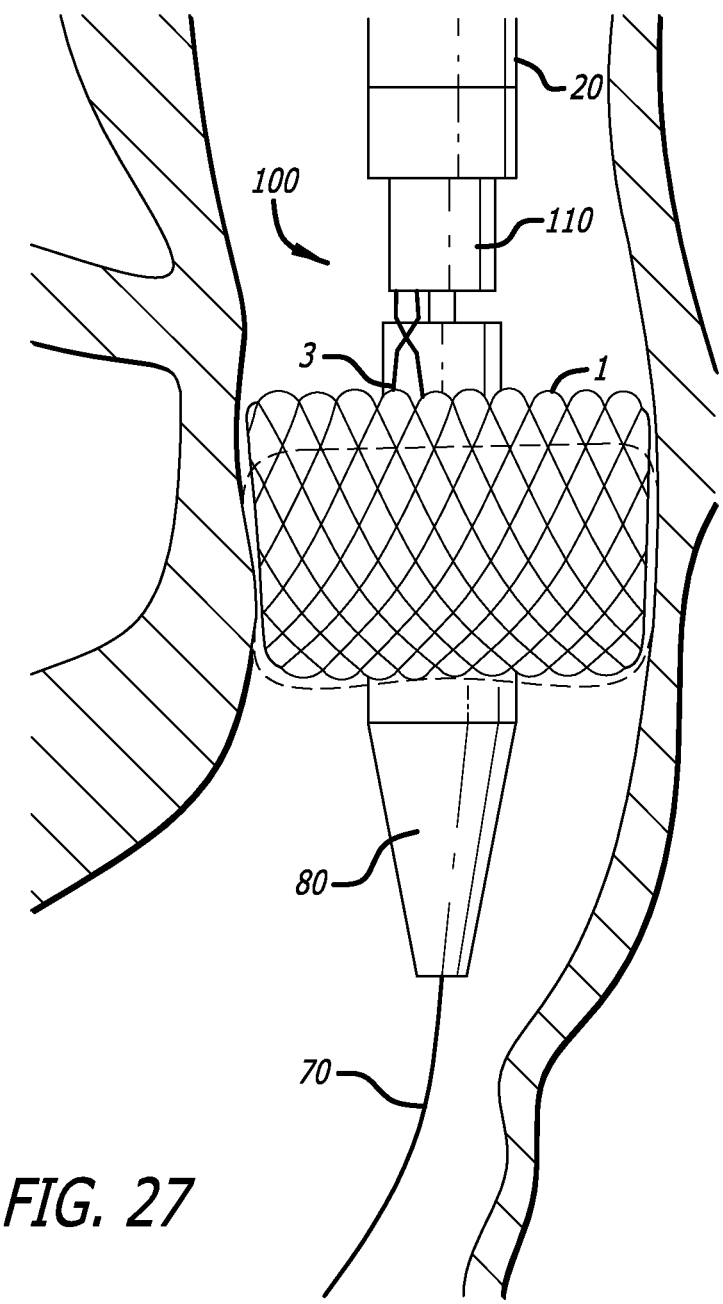
FIG. 27 is a side view of an embodiment of a delivery device as shown in FIG. 22, just after releasing and withdrawing the tethers from the implant.

As shown in FIG. 25, next, the implant 1 is folded or inverted on itself by restraining the implant with the tethers 104 and pushing a proximal portion of the implant in a distal direction with the pusher catheter 110. More specifically, when the first layer of the implant has been deployed, the tether positioning mechanism 340 will have reached the delivery catheter manifold. This freezes the position of the ventricular loops (the distal end) of the implant such that further advancement of the implant will result in a shortening and flaring of the implant in preparation for valve invention.

This flaring aspect of the valve deployment has been described as the anchoring phase, as the implant has expanded to contact the native valve tissue and the aortic flare of the device provides substantial resistance to migration. Once the anchoring phase has begun, the delivery catheter 20 is advanced through the access site and the patient vasculature. Doing so aligns the distal tip of the delivery catheter coaxial to the native valve with the curve of the delivery catheter 20 filling the outer curvature of the native aortic arch.

After the catheter 20 has been advanced, continued deployment of the valve using the drive knob is used to produce implant invention. The act of inverting the implant also deploys the tissue valve component of the implant. Once the implant has been inverted the valve begins to function, but that function is somewhat constrained due to the proximity of the tethers and the valve control cables.

After inversion has been accomplished, the user releases the tethers. First the tether positioning mechanism 340 is released by releasing the lever 344, separating it from the clamp block 346. The tether positioning mechanism 340 is free to float along the outer tether sheath 112. The drive knob 268 is rotated to further back the delivery catheter 20 away from the implant. Once the delivery catheter 20 is fully retracted, the tethers 104 can be removed by rotating and releasing the tension in the control knob 314 of the tether release controller 310. Gently pulling on the tether release controller 310 will separate the tethers 104 from the implant.

Figure 28:
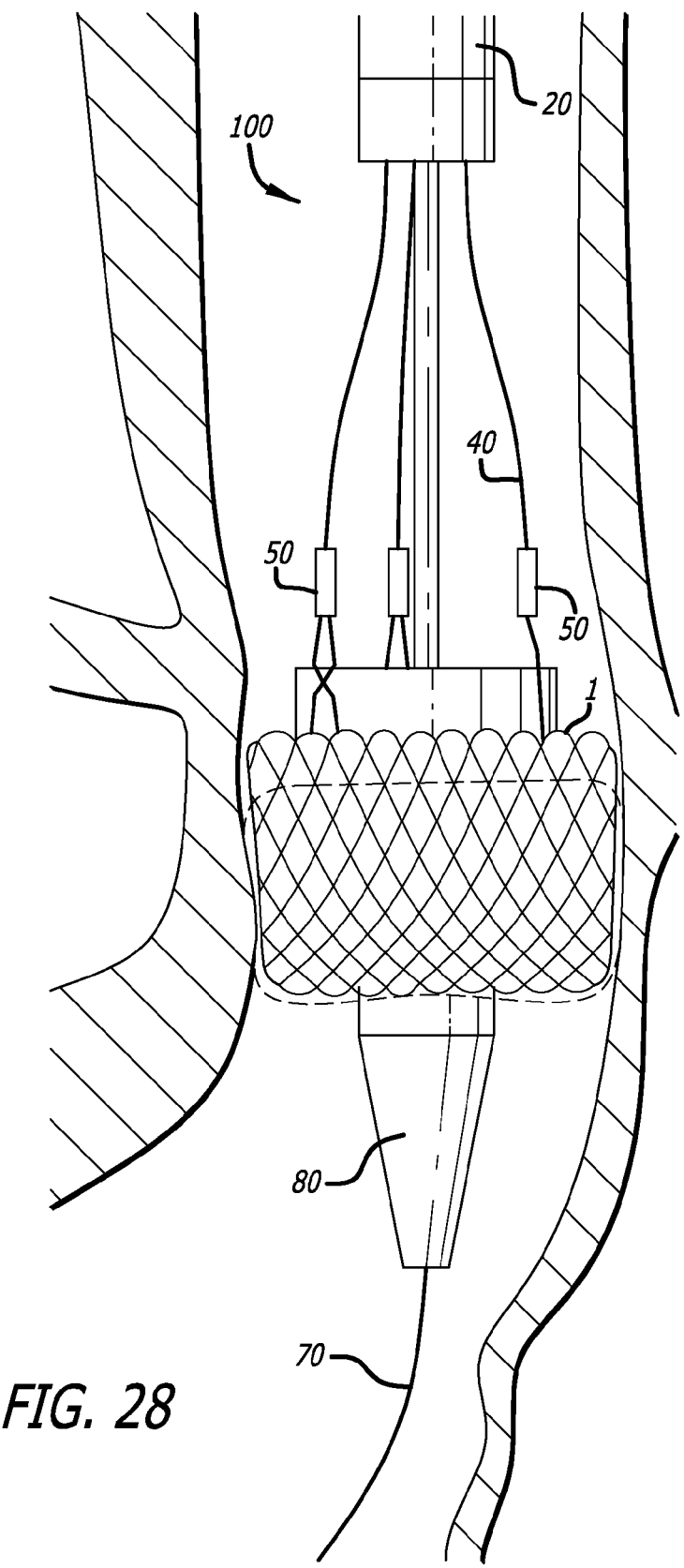
FIG. 28 is a side view of an embodiment of a delivery device as shown in FIG. 22, just prior to releasing the attachment cables; and, FIG. 29 is a side view of an embodiment of the implant, just after release of the attachment cables.

Once the tethers 104 have been removed, only the valve retention cables 40 remain connected to the implant 1, as seen in FIG. 28. As previously discussed, these cables 40 are attached to a proximal feature on the implant (e.g., the commissural points) and allow the physician to completely retract the implant 1 back into the delivery device 100 if a problem arises during the delivery procedure. Specifically, in order to observe full valve function without releasing the implant, the physician beings by rotating the ring 250 away from the operator and sliding the ring 250 in a proximal direction, retracting the pusher catheter 30. With the pusher catheter 30 retracted, the prosthetic valve now begins to function fully. The remaining attachment of the delivery system to the implant via the valve retention cables 40 has little effect on the functionality of the implant.

Once satisfied, the physician next releases the implant by pulling the locking pin 216 at the proximal end of the handle assembly 200. With the locking pin 216 removed, each of the three valve retention cable controllers 212 can be sequentially released. This is accomplished by depressing the catch 222 and sliding the thumb slide 220 forward, releasing the implant 1. Each cable can be individually retracted into the delivery catheter after it has been disengaged. When all three cables are released, the valve is fully implanted and the delivery system may be removed from the vascular introducer of the patient.

Figure 29:
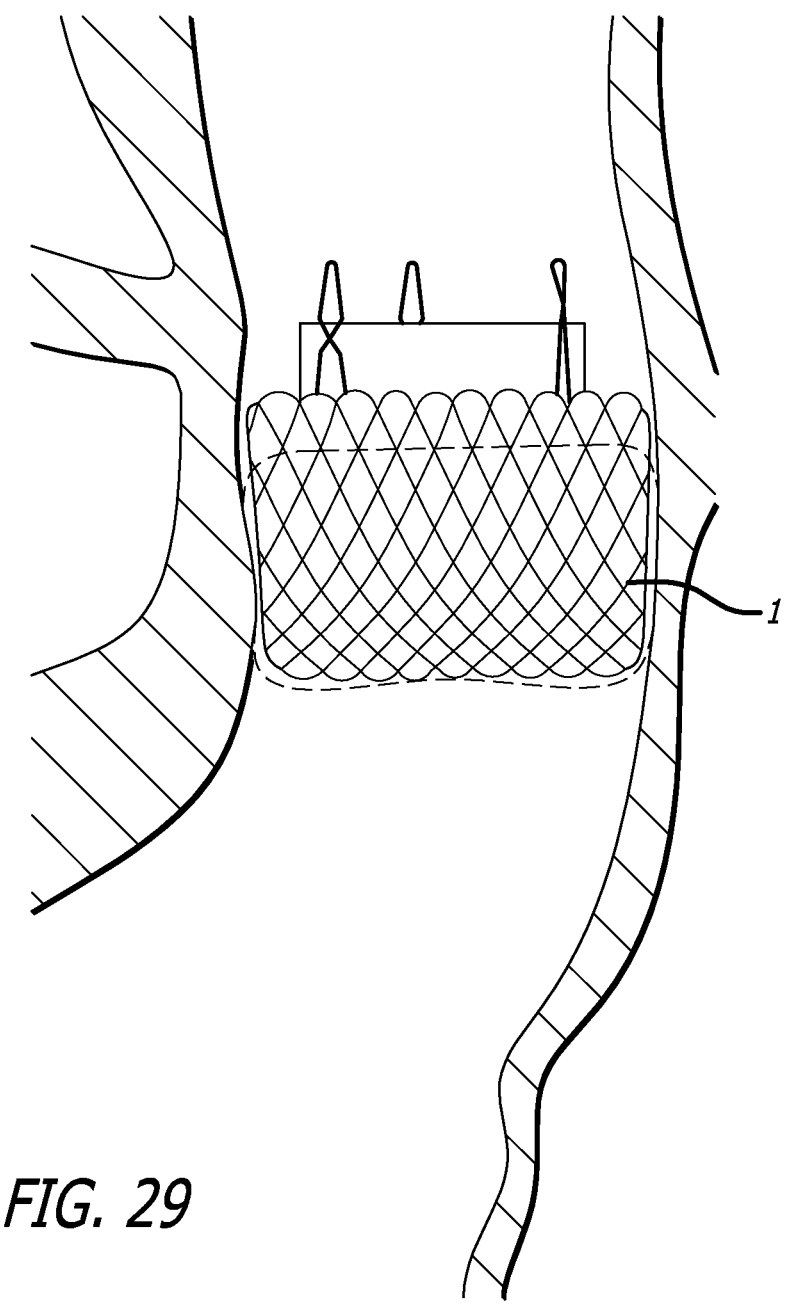

Finally, the delivery device 100 and guidewire 70 is removed from the patient, leaving only the functioning valve implant 1, as seen in FIG. 29.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A delivery device for deployment of an implant comprising:
   a handle;
   a catheter extending from a distal end of said handle, said catheter including a delivery catheter and a pusher catheter slidingly disposed within said delivery catheter;
   a drive mechanism attached to said pusher catheter and said delivery catheter and including a control knob and a threaded shaft such that rotation of said control knob results in axial movement of said threaded shaft, said axial movement of said threaded shaft effecting relative axial movement between said pusher catheter and said delivery catheter, wherein said delivery catheter is fixed to said distal end of said threaded shaft;
   a quick release mechanism associated with said control knob, said quick release mechanism disengaging said drive mechanism such that said threaded shaft may be moved axially without rotation, wherein said quick release mechanism comprises a button on said control knob, and wherein said threaded shaft includes interrupted helices that form a longitudinal slide over which said quick release mechanism rides when said button is pushed.

2. The delivery device of claim 1 wherein said quick release mechanism comprises a lever on said control knob.

3. The delivery device of claim 1 further comprising a locking mechanism associated with said pusher catheter for locking and unlocking said pusher catheter relative to said handle.

4. The delivery device of claim 1 further comprising a plurality of cables aligned within a plurality of associated lumens of said pusher catheter, said cables releasably attaching an implant to said delivery device.

5. An implant delivery device comprising:
   a handle;
   a lead screw axially moveable relative to said handle;
   a threaded nut combination in driving relationship to said lead screw and including:
   a knob axially fixed relative to said handle;
   a threaded nut contained within said knob;
   whereby rotation of said knob causes said nut to act against said lead screw;
   a quick release mechanism capable of disengaging said threaded nut from threads of said lead screw, said quick release mechanism including a flat axial interruption in said threads of said lead screw.

6. The implant delivery device of claim 5 wherein said quick release mechanism comprises a button.

7. The implant delivery device of claim 6 wherein said button is located on said knob.

* * * * *